(12) United States Patent
Chon et al.

(10) Patent No.: US 9,713,428 B2
(45) Date of Patent: Jul. 25, 2017

(54) PHYSIOLOGICAL PARAMETER MONITORING WITH A MOBILE COMMUNICATION DEVICE

(75) Inventors: Ki H. Chon, Worcester, MA (US); Jinseok Lee, Worcester, MA (US); Nandakumar Selvaraj, Worcester, MA (US)

(73) Assignee: Worcester Polytechnic Institute, Worcester, MA (US)

( * ) Notice: Subject to any disclaimer, the term of this patent is extended or adjusted under 35 U.S.C. 154(b) by 94 days.

(21) Appl. No.: 13/354,941

(22) Filed: Jan. 20, 2012

(65) Prior Publication Data

US 2012/0190947 A1 Jul. 26, 2012

Related U.S. Application Data

(60) Provisional application No. 61/434,862, filed on Jan. 21, 2011, provisional application No. 61/512,199, filed on Jul. 27, 2011, provisional application No. 61/434,856, filed on Jan. 21, 2011, provisional application No. 61/566,329, filed on Dec. 2, 2011.

(51) Int. Cl.
*A61B 5/00* (2006.01)
*A61B 5/024* (2006.01)
*A61B 5/0452* (2006.01)
*A61B 5/08* (2006.01)
*A61B 5/1455* (2006.01)

(52) U.S. Cl.
CPC ...... *A61B 5/02405* (2013.01); *A61B 5/02416* (2013.01); *A61B 5/0452* (2013.01); *A61B 5/0816* (2013.01); *A61B 5/14551* (2013.01); *A61B 5/7207* (2013.01)

(58) Field of Classification Search
CPC ... A61B 5/1455; A61B 5/0002; A61B 5/0004; A61B 5/145; A61B 5/14551; A61B 5/0059; A61B 5/14552; A61B 5/0205; A61B 5/02405
USPC ....... 600/300, 301, 309, 310, 322, 323, 324, 600/326, 330, 336, 473, 476, 500, 501, 600/502, 508, 509, 518
See application file for complete search history.

(56) References Cited

U.S. PATENT DOCUMENTS

| | | | | |
|---|---|---|---|---|
| 6,067,462 | A * | 5/2000 | Diab et al. | 600/310 |
| 6,159,147 | A * | 12/2000 | Lichter et al. | 600/300 |
| 6,198,394 | B1 * | 3/2001 | Jacobsen et al. | 340/573.1 |
| 6,678,548 | B1 * | 1/2004 | Echauz et al. | 600/544 |
| 6,879,850 | B2 * | 4/2005 | Kimball | 600/336 |

(Continued)

FOREIGN PATENT DOCUMENTS

| | | |
|---|---|---|
| WO | 9932030 A1 | 7/1999 |
| WO | 2009024273 A1 | 2/2009 |

OTHER PUBLICATIONS

Muthuswamy et al., "Spectral analysis methods for neurological signals", Journal of Neuroscience Methods 83 (1998) 1-14.*

(Continued)

*Primary Examiner* — Eric Winakur
*Assistant Examiner* — Chu Chuan (JJ) Liu
(74) *Attorney, Agent, or Firm* — Burns & Levinson LLP; Orlando Lopez

(57) ABSTRACT

Systems and methods that enable physiological monitoring with a mobile communication device and that allow detection of motion artifacts so that the results reported are of acceptable quality are disclosed.

46 Claims, 10 Drawing Sheets

(56) References Cited

U.S. PATENT DOCUMENTS

| | | | |
|---|---|---|---|
| 7,254,425 | B2 | 8/2007 | Lowery et al. |
| 2003/0036685 | A1 | 2/2003 | Goodman |
| 2005/0070774 | A1* | 3/2005 | Addison et al. .............. 600/323 |
| 2006/0122476 | A1 | 6/2006 | Van Slyke |
| 2006/0135860 | A1 | 6/2006 | Baker et al. |
| 2006/0211930 | A1 | 9/2006 | Scharf et al. |
| 2006/0253261 | A1* | 11/2006 | Maier et al. .................... 702/19 |
| 2007/0078316 | A1 | 4/2007 | Hoarau et al. |
| 2007/0213624 | A1* | 9/2007 | Reisfeld ............ A61B 5/14551 600/504 |
| 2009/0112110 | A1* | 4/2009 | Zhang ........................... 600/518 |
| 2010/0030088 | A1 | 2/2010 | Carney et al. |
| 2010/0150375 | A1* | 6/2010 | Buck et al. .................. 381/94.1 |

OTHER PUBLICATIONS

International Search Report dated Jun. 28, 2012 from co-pending PCT/US2012/022049, filed on Jan. 20, 2012, which claims the benefit of U.S. Appl. No. 61/434,856, filed Jan. 21, 2011.
Written Opinion from the International Searching Authority from co-pending PCT/US2012/022049, filed on Jan. 20, 2012, which claims the Benefit of U.S. Appl. No. 61/434,856, filed Jan. 21, 2011.
Krishnan, R. et al. Analysis and detection of motion artifact in photoplethysmographic data using higher order statistics. IEEE International Conference on Acoustics, Speech and Signal Processing, Mar. 2008: 613-616.
Krishnan, R. et al. Two-Stage Approach for Detection and Reduction of Motion Artifacts in Photoplethysmographic Data. IEEE Transactions on Biomedical Engineering 57(8), Aug. 2010: 1867-1876.
Greco, A. et al. Kurtosis, Renyi's Entropy and Independent Component Scalp Maps for the Automatic Artifact Rejection from EEG data. International Journal of Computer, Information, Systems and Control Engineering 2(9), Jan. 2008: 180-184.
Delorme, A. et al. Enhanced detection of artifacts in EEG data using higher-order statistics and independent component analysis. Neuroimage 34(4), Feb. 2007: 1443-1449.
Delorme, A. et al. Automatic Artifact Rejection for EEG Data Using High-Order Statistics and Independent Component Analysis, Jan. 2001. Available at: www.inc2.ucsd.edu.
Chon, K.H. Estimation of Respiratory Rate from Photoplethysmogram Data Using Time-Frequency Spectral Estimation. IEEE Transactions of Biomedical Engineering, 56(8), Aug. 2009: 2054-2063.
Middleton, P.M. et al. Spectral Analysis of Finger Photoplethysmogram Waveform Variability in a Model of Mild to Moderate Haemorrhage. Journal of Clinical Monitoring and Computing (2008) 22:343-353.
Pelegris, P. et al. A Novel Method to Detect Heart Beat Rate Using a Mobile Phone. Proceeding of the IEEE 32nd Annual International Conference, Aug. 2010: 5488-5491.
Barbati et al. "Optimization of an Indepedent Component Analysis Apporach for Artifact Identification and Removal in Magnetoencephalographic Signals." Clin. Neurophys. 115(2004):1220-1232.
Rajet Krishnan et al; "Analysis and Detection of Motion Artifact in Photoplethysmographic Data Using Higher Order Statistics"; Acoustics, Speech and Signal Proceeding, IEEE 2008; pp. 613-616.
Delorme, A. et al; SNL, Salk University; "Automatic Artifact Rejection for EEG Data Using High-Order Statistics and Independent Component Analysis"; Proceedings of the 3rd International Workshop on ICA; San Diego, 2001; pp. 457-462.
Third Office Action (English translation also enclosed) dated Feb. 29, 2016 in corresponding Chinese Application No. 201280014031.1, filed on Jan. 20, 2012.

* cited by examiner

2a
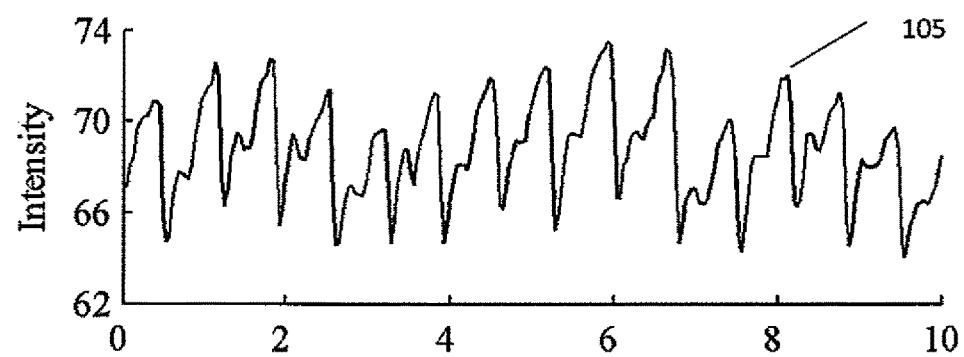
2b
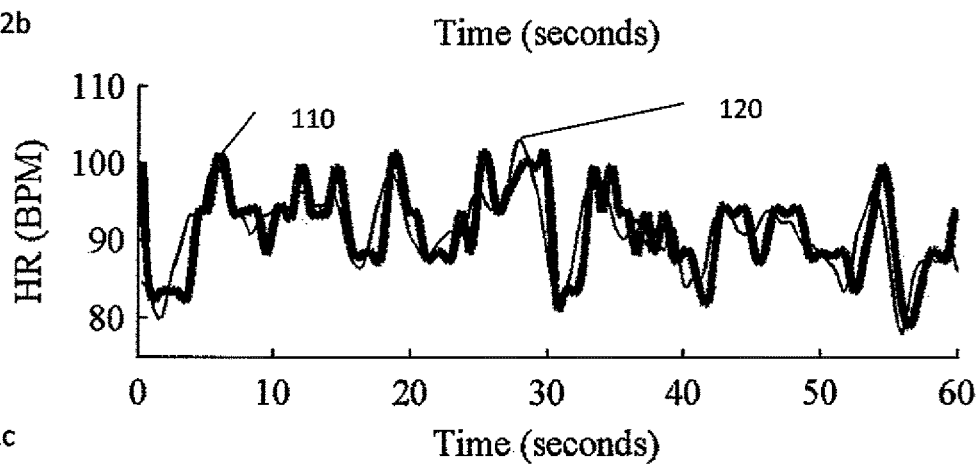
2c
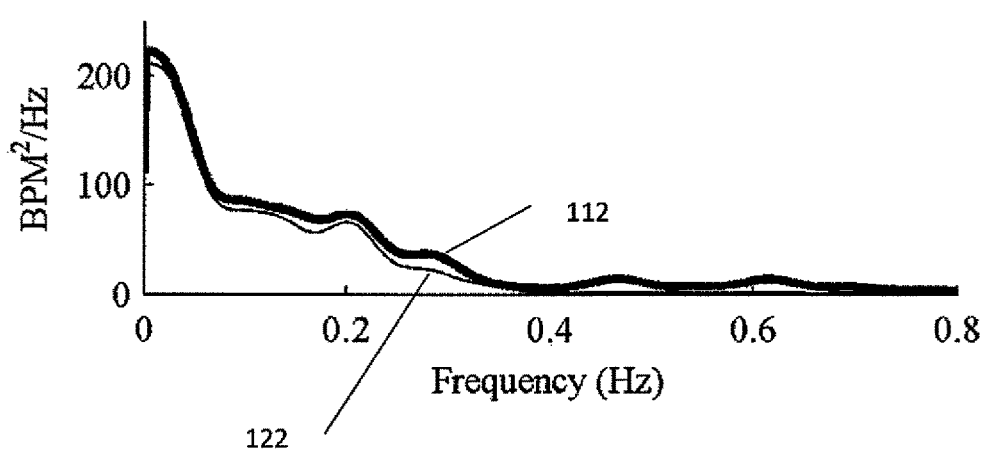
Figs. 2a-c

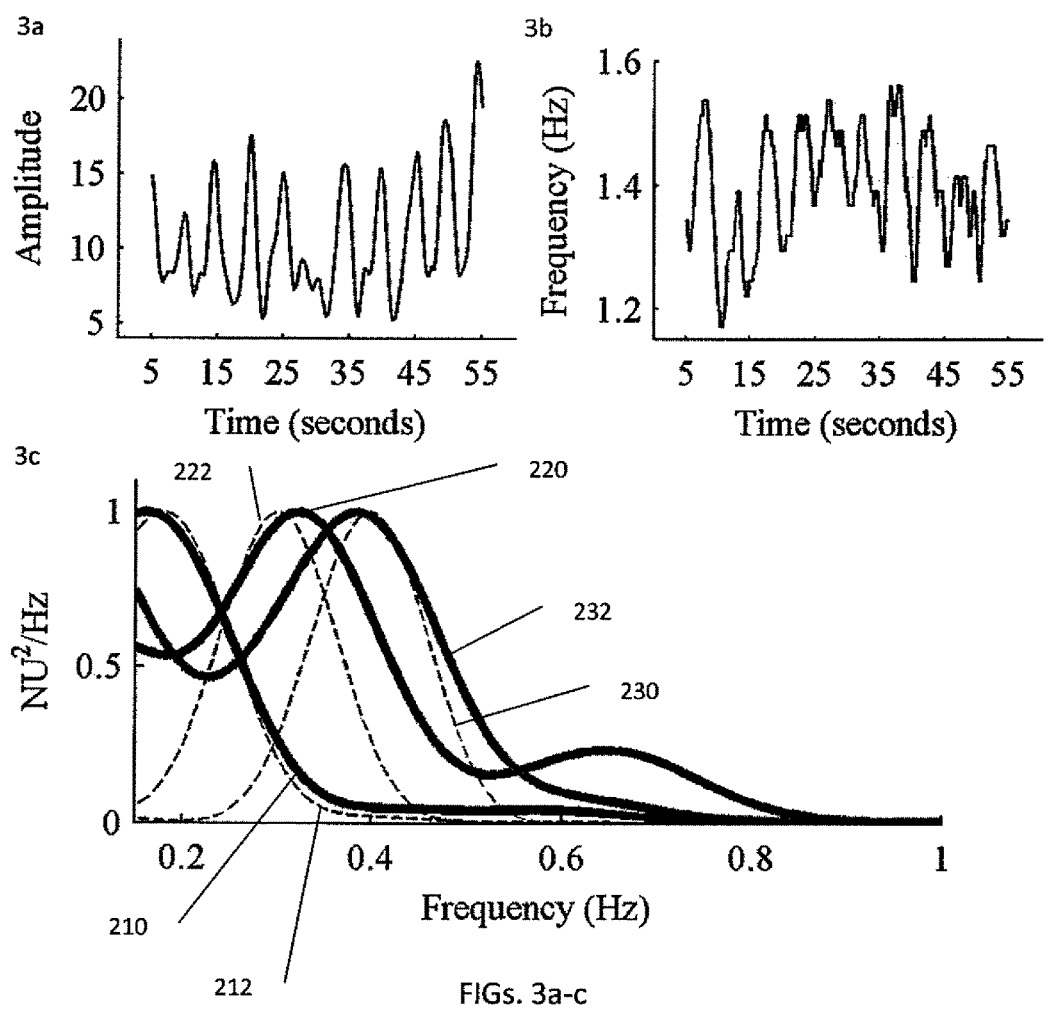
FIGs. 3a-c

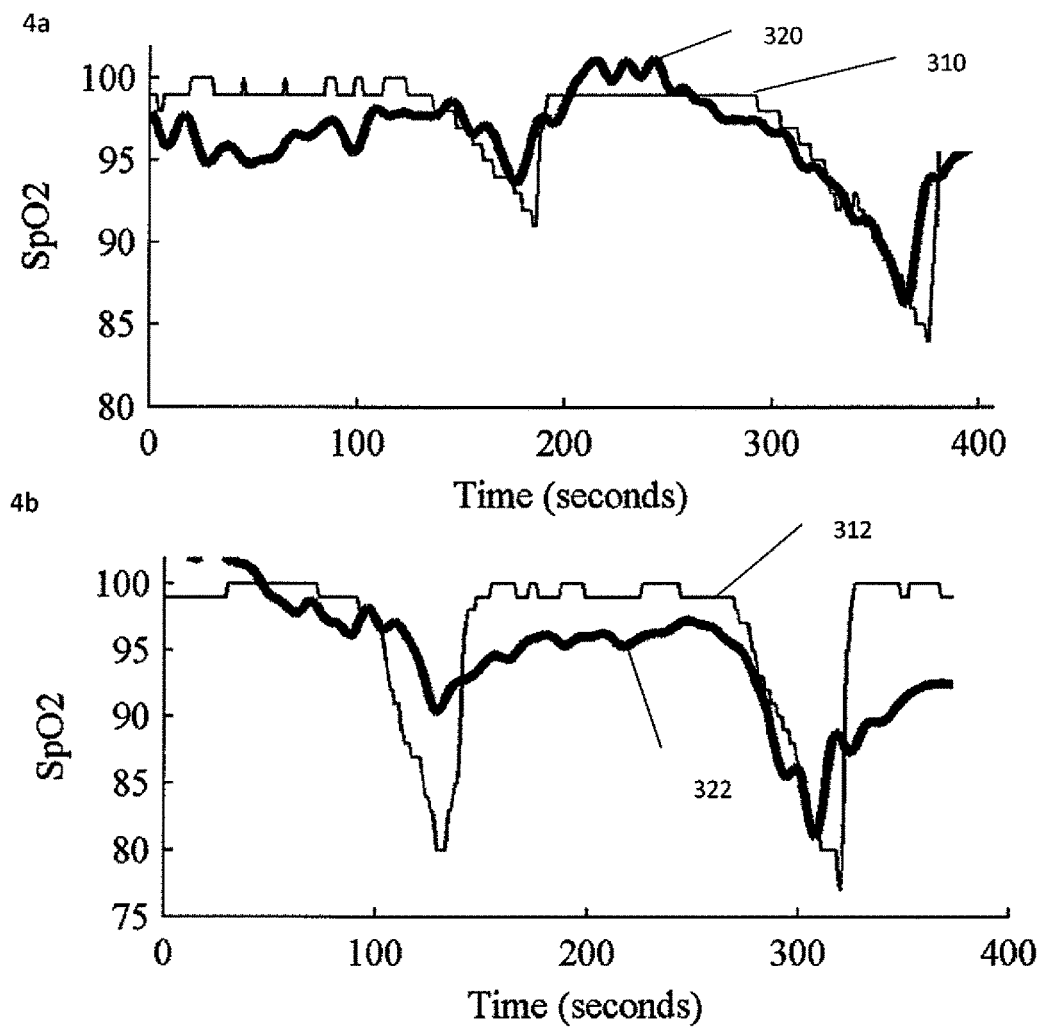
Figs. 4a-b

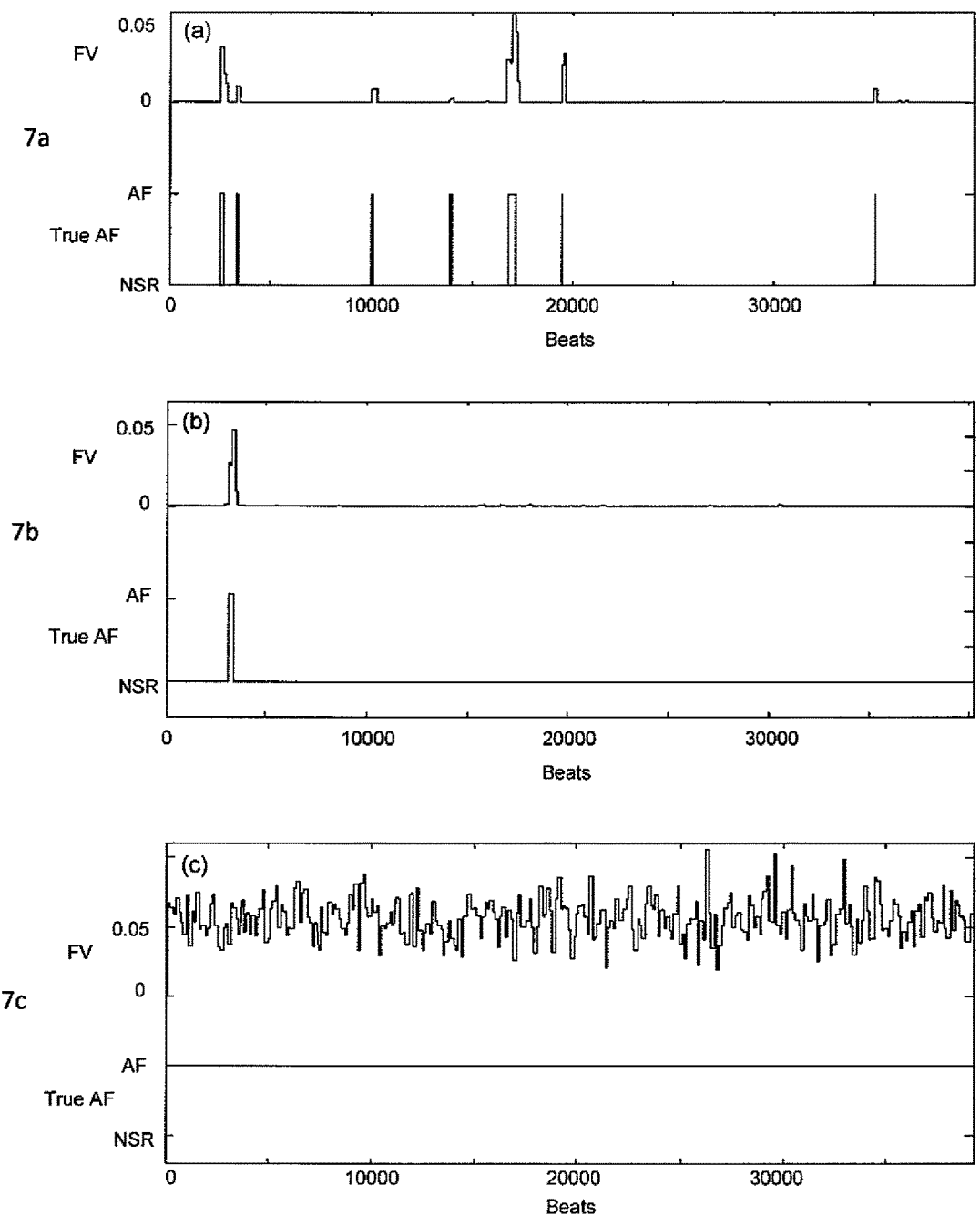
Figs. 7a-c

PHYSIOLOGICAL PARAMETER MONITORING WITH A MOBILE COMMUNICATION DEVICE

CROSS REFERENCE TO RELATED APPLICATIONS

This application claims priority to U.S. Provisional Application Ser. No. 61/434,862, filed Jan. 21, 2011, entitled, "SYSTEM FOR QUANTIFYING THE PRESENCE OF PHASE COUPLING USING THE BISPECTRUM," U.S. Provisional Application Ser. No. 61/512,199, filed Jul. 27, 2011, entitled, "PHYSIOLOGICAL PARAMETER MONITORING FROM OPTICAL RECORDINGS WITH A MOBILE PHONE," U.S. Provisional Application Ser. No. 61/434,856, filed Jan. 21, 2011, entitled, SYSTEM AND METHOD FOR THE DETECTION OF BLOOD VOLUME LOSS," and U.S. Provisional Application Ser. No. 61/566,329, filed Dec. 2, 2011, entitled, "TIME-VARYING COHERENCE FUNCTION FOR ATRIAL FIBRILLATION DETECTION," all of which are incorporated by reference herein in their entirety for all purposes.

STATEMENT REGARDING FEDERALLY SPONSORED RESEARCH OR DEVELOPMENT

This work was funded in part by the Office of Naval Research, Work Unit N00014-10-1-0640. The U.S. Government has certain rights in the invention.

BACKGROUND

These teachings relate generally to physiological parameter monitoring, and, more particularly, to physiological parameter monitoring with a mobile communication device.

There is a need for low-cost physiological monitoring solutions that are easy to use, accurate, and can be used in the home or in ambulatory situations. Smart phones are becoming more popular, more powerful and have a variety of sensors available to capture information from the outside world, process in real-time, and transfer information remotely using wireless communications. This makes them an ideal option as a 'take-anywhere' physiological monitor without the need for additional hardware, and their potential has been explored for many medical telemonitoring applications.

Optical video monitoring of the skin with a digital camera contains information related to the subtle color changes caused by the cardiac signal and can be seen to contain a pulsatile signal. Given illumination of the area with a white LED mobile phone flash, this type of imaging can be described as reflection photoplethysmographic (PPG) imaging. The dynamics of the HR signal that can be captured by PPG contain information that can be used to detect other physiological conditions.

Motion artifacts can affect the results of standard PPG. In the case of a mobile device and where there is no physical device ensuring a stable connection as is the case with pulse-oximeter clips or EKG electrodes, motion artifacts can be of more concern. There is a need for systems and methods for physiological monitoring with a mobile communication device that allow detection of motion artifacts.

BRIEF SUMMARY

The teachings described herein disclose systems and methods that enable physiological monitoring with a mobile communication device and that allow detection of motion artifacts so that the results reported are of acceptable quality are disclosed.

In one or more embodiments, the method of these teachings for physiological parameter monitoring includes providing a physiological indicator signal to a mobile communication device analyzing, using the mobile communications device, the physiological indicator signal to obtain measurements of one or more physiological parameters and detecting, using the mobile communications device, effects of motion artifacts in the measurements of the one or more physiological parameters and deciding whether to retain the measurements.

Other embodiments and instances of the method of these teachings are also disclosed.

In one or more embodiments of the system of these teachings, the system includes a physiological indicator signal sensing component (sensor) and a mobile communication device having an analysis component analyzing the physiological indicator signal to obtain measurements of one or more physiological parameters and a motion artifact detection component detecting effects of motion artifacts in the measurements of the one or more physiological parameters.

Other embodiments and instances of the system of these teachings are also disclosed.

Embodiments and instances of computer usable media having computer readable code embodied therein, where the computer readable code causes one or more processors to implement the embodiments of the method of these teachings are also disclosed.

For a better understanding of the present teachings, together with other and further objects thereof, reference is made to the accompanying drawings and detailed description and its scope will be pointed out in the appended claims.

BRIEF DESCRIPTION OF THE DRAWINGS

FIGS. 2a-2c are schematic graphical representations of results for one exemplary embodiment of the method of these teachings;

FIGS. 3a-3c are schematic graphical representations of results for another exemplary embodiment of the method of these teachings;

FIGS. 4a-4b are schematic graphical representations of results for yet another exemplary embodiment of the method of these teachings;

FIGS. 7a-7c illustrate schematic graphical representations of true AF annotation and the values of frequency variations (FV) for different databases in the further exemplary embodiment of the method of these teachings.

DETAILED DESCRIPTION

The following detailed description is of the best currently contemplated modes of carrying out these teachings. The description is not to be taken in a limiting sense, but is made merely for the purpose of illustrating the general principles of these teachings, since the scope of these teachings is best defined by the appended claims. Although the teachings have been described with respect to various embodiments, it should be realized these teachings are also capable of a wide variety of further and other embodiments within the spirit and scope of the appended claims.

As used herein, the singular forms "a," "an," and "the" include the plural reference unless the context clearly dictates otherwise.

Except where otherwise indicated, all numbers expressing quantities of ingredients, reaction conditions, and so forth used in the specification and claims are to be understood as being modified in all instances by the term "about."

To assist in the understanding of the present teachings the following definitions are presented.

A "mobile communication device," as used herein, refers to a device capable of executing applications, and which is portable. In one instance, the mobile communication device has one or more processors and memory capability. Examples of mobile communication devices, these teachings not being limited to only these examples, include mobile phones, smart mobile phones, digital personal assistants, etc.

A "physiological indicator signal," as used herein, refers to a signal that can be used to obtain measurements of one or more physiological parameters. Examples of physiological indicator signals, these teachings not being limited only to those examples, include photoplethysmograph (PPG) signals, electrocardiogram (EKG) signals and color video images obtained from a portion of a subject's body (for example, but not limited to, obtained using the camera in a mobile communication device), which behave as reflection PPG images.

"Volatility," as used herein, refers to a measure of the probability of obtaining an extreme value in the future, such as measured by kurtosis and other statistical measures.

"Detrending," as used herein, refers to the process of finding a best polynomial fit to a time series and subtracting that best polynomial fit from the time series.

"SpO2," as used herein, refers to a measurement of the amount of oxygen being carried by the red blood cell in the blood. SpO2 is usually given in as a percentage and measures oxygen saturation.

Figure 1:
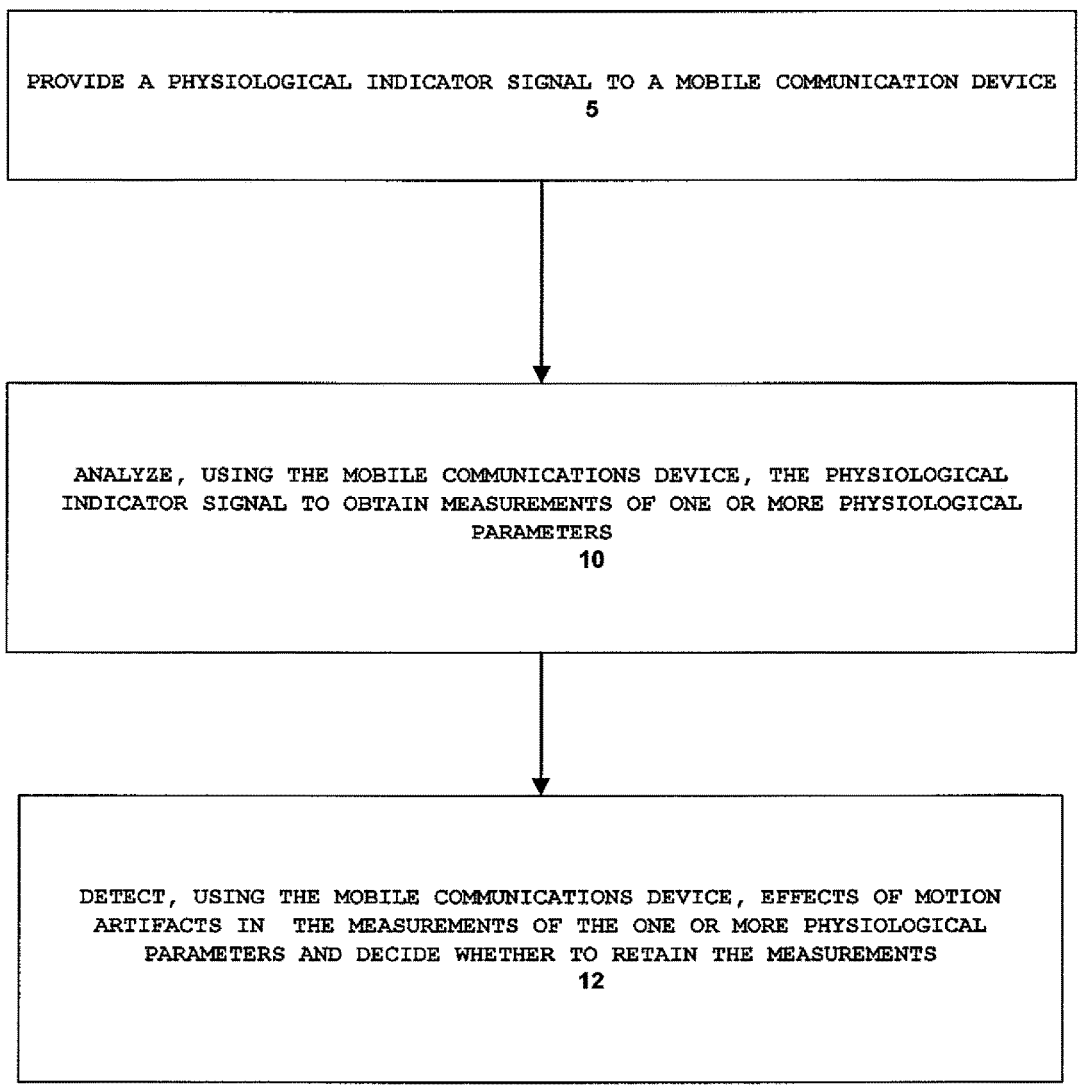
FIG. 1 is a flowchart representation of one embodiment of the method of these teachings.

In one or more embodiments, the method of these teachings for physiological parameter monitoring includes providing a physiological indicator signal to a mobile communication device (step 5, FIG. 1), analyzing, using the mobile communications device, the physiological indicator signal to obtain measurements of one or more physiological parameters (step 10, FIG. 1) and detecting, using the mobile communications device, effects of motion artifacts in the measurements of the one or more physiological parameters and deciding whether to retain the measurements (step 12, FIG. 1).

The physiological indicator signal can, in one instance, be provided by placing a portion of a subject's body over an objective lens of a camera in a mobile communication device and obtaining video images of the portion of the subject's body. In another instance, the physiological indicator signal can be provided by a physiological monitoring sensor, for example, an external photoplethysmographic (PPG) sensor or an external electrocardiogram sensor. It should be noted that other manners of providing the physiological indicator signal are within the scope of these teachings.

Motion Artifacts

One embodiment of the method for detecting effects of motion artifacts in the measurements of the one or more physiological parameters and deciding whether to retain the measurements is disclosed hereinbelow. It should be noted that other embodiments are within the scope of these teachings.

Figure 1A:
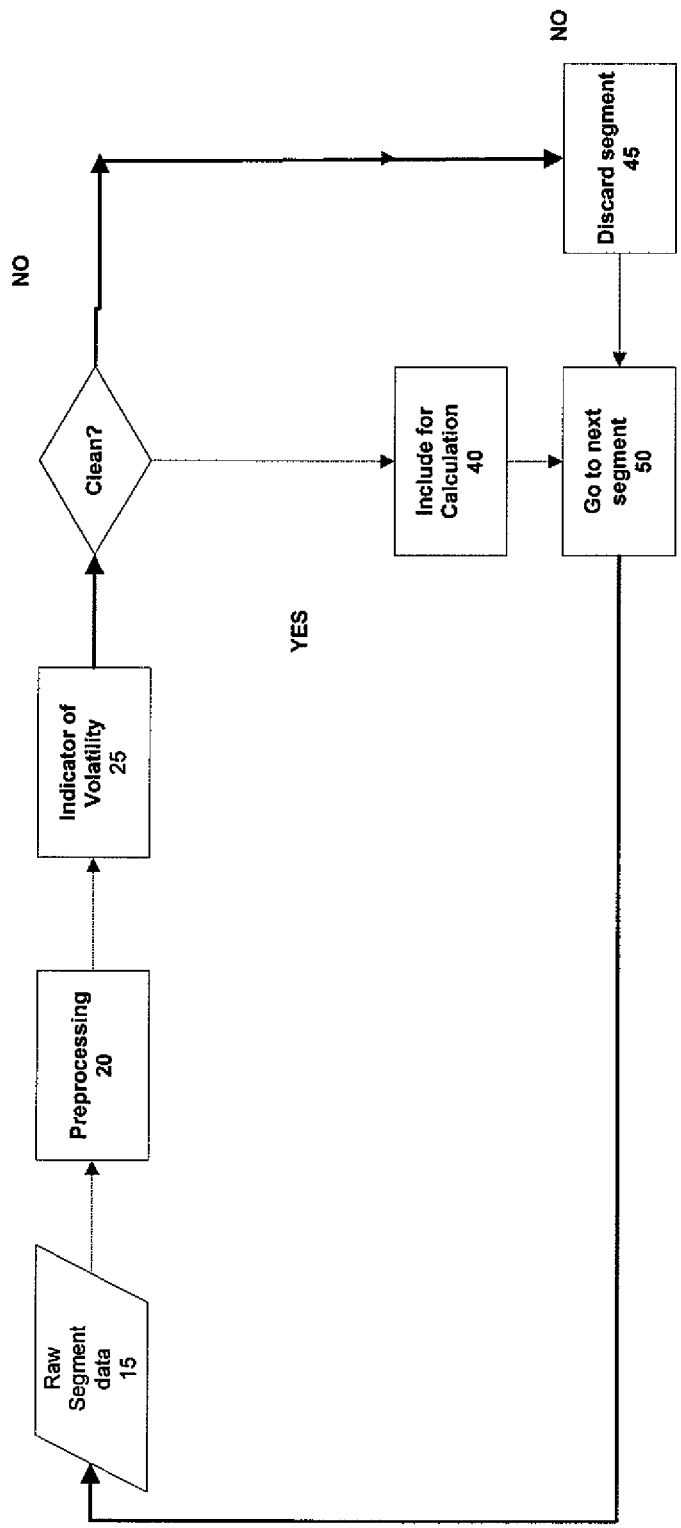
FIG. 1a is a schematic flowchart representations of components of one embodiment of the method of these teachings.
Figure 1B:
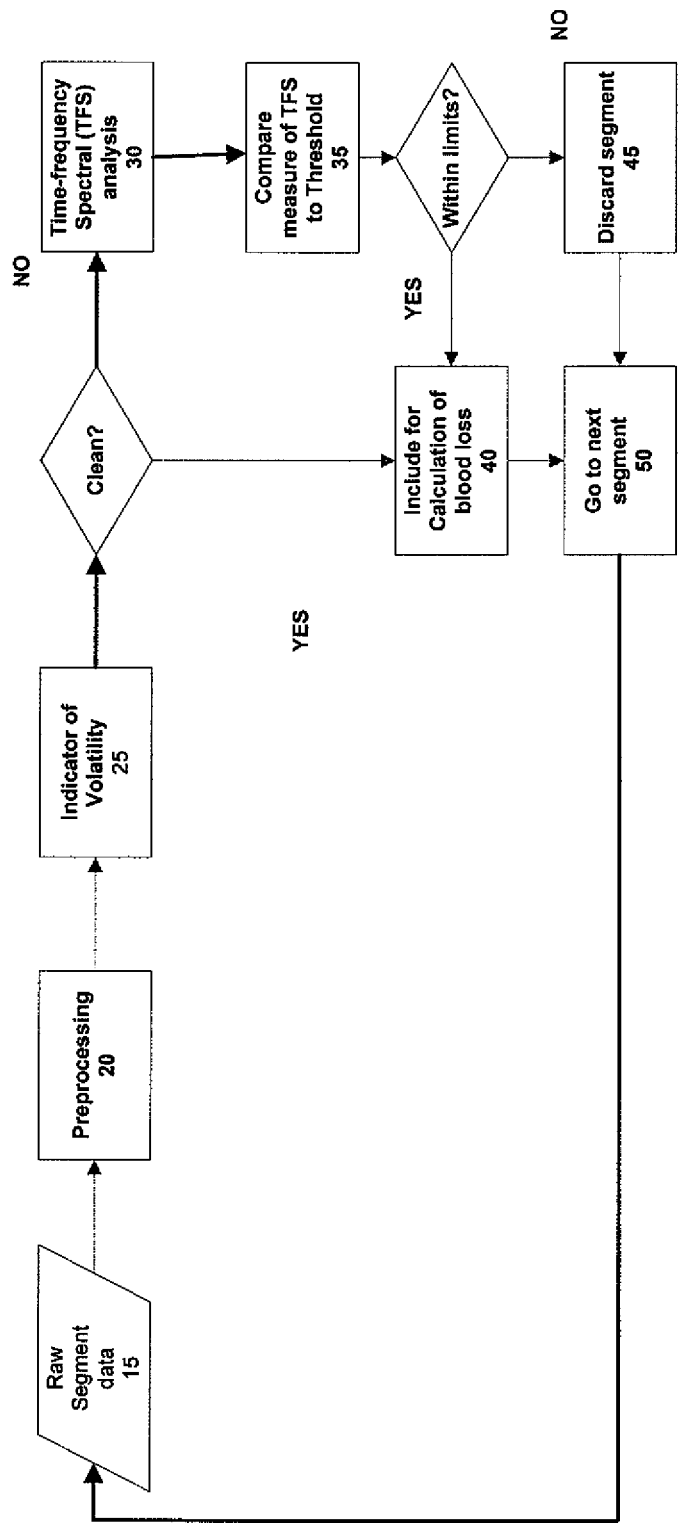
FIG. 1b is a schematic flowchart representations of components of another embodiment of the method of these teachings.

In the embodiment shown in FIG. 1a, the method for detecting effects of motion artifacts includes preprocessing a segment of a signal (15, FIG. 1a) from a physiological measurement (29, FIG. 1a), obtaining a value of one or more indicators of volatility for the preprocessed segment (25, FIG. 1a) and determining from comparison of the value of the one or more indicators of volatility with a predetermined threshold whether or not noise/motion artifacts are not present. If noise/motion artifacts are not present, the segment is included in calculations quantities of interest (40, FIG. 1a) and the method proceeds to another segment (50, FIG. 1a), if another segment is available. If noise/motion artifacts are present, for most physiological parameters, the segment is discarded (45, FIG. 1a) and the method proceeds to another segment (50, FIG. 1a), if another segment is available. For the measurement of an indication of blood loss, as shown in FIG. 1b, a time-frequency spectrum analysis is performed for the preprocessed segment (30, FIG. 1b) and a predetermined measure of the time-frequency spectrum analysis is compared to a predetermined measure's threshold (35, FIG. 1b). If the predetermined measure is within limits determined by the predetermined measure's threshold, the segment is included in calculations quantities of interest (40, FIG. 1b) and the method proceeds to another segment, if another segment is available (50, FIG. 1b). If the predetermined measure is not within the limits determined by the predetermined measure's threshold, the segment is discarded (45, FIG. 1b) and the method proceeds to another segment (50, FIG. 1b), if another segment is available.

In one instance, the measure of volatility used in the above disclosed embodiment includes kurtosis. In another instance, the measure of volatility includes Shannon entropy. In a further instance, the measure of volatility uses both kurtosis and Shannon entropy.

An exemplary embodiment of the application of the method for detecting motion artifacts is described herein below in order to further elucidate these teachings. However it should be noted that these teachings are not limited to only that exemplary embodiments.

Experimental Protocol for One Exemplary Embodiment

The algorithm has been tested on PPG signals obtained from two distinct scenarios as follows.

1. Involuntary movements: Multi-site PPG signals recorded from 10 healthy volunteers under supine resting conditions for 5 to 20 minutes in clinical settings were used for our analysis. The data analyzed were a part of simulated blood loss experiments which consisted of baseline and lower body negative pressure application where the data from only the former condition was used for this study. Three identical reflective infrared PPG-probes (MLT1020; ADI Instruments, CO Springs, Colo., USA) were placed at the finger, forehead and ear. While the finger and ear PPG probes were attached with a clip, the forehead probe was securely covered by a clear dressing. The PPG signals were recorded at 100 Hz with a Powerlab/16 SPdata acquisition system equipped with a Quad Bridge Amp (ML795 & ML112; ADI Instruments) and a high-pass filter cut-off of 0.01 Hz. The subjects were not restricted from making any sort of movements during the recording procedure.

2. Voluntary movements: Finger-PPG signals were obtained from 14 healthy volunteers in an upright sitting posture using an infrared reflection type PPG transducer (TSD200) and a biopotential amplifier (PPG100) with a gain of 100 and cut-off frequencies of 0.05-10 Hz. The MP100 (BIOPAC Systems Inc., Calif., USA) was used to acquire finger PPG signals at 100 Hz. After baseline recording for 5 minutes without any movements (i.e. clean data), motion artifacts were induced in the PPG data by left-right movements of the index finger with the pulse oximeter on it. The subjects were directed to produce the motions for time intervals that determined the percentage of noise within each 1 minute segment; varying from 10 to 50%. For example, if a subject was instructed to make left-right movements for 6 seconds, that segment of data would contain 10% noise. Such controlled movements were carried out 5 times for each level of noise. In this protocol, we used the left-right movement of the index finger having the PPG clamp to induce movement artifacts since left-right movement was perpendicular to the plane of the PPG sensor orientation and thus generated significant noise as compared to up-down or arbitrary movements of the finger. The recorded PPG signals from both protocols were analyzed offline using Matlab®.

B. Data Preprocessing:

The PPG data were partitioned into 60 s segments and shifted every 10 s for the entire data. Each 60 s PPG segment was subjected to a finite impulse response (FIR) band pass filter of order 64 with cut-off frequencies of 0.1 Hz and 10 Hz. To account for the time-dependent low-frequency trends associated with the PPG signal and depending on the type of data analysis, either a low- or high-order polynomial detrending was used. For the purpose of artifact detection, we used in some cases as high as the 32nd-order polynomial fit to eliminate nonstationary dynamics in the PPG signal. The use of a high-order polynomial detrend is important to an effective classification between clean and artifact-containing signals. For the time-frequency-spectral analysis during the second stage to determine usable data, a standard 2nd order polynomial detrend was used on the original PPG data (not on the data with a high-order polynomial detrend). Following detrend with either a low- or high-order polynomial fit, the PPG signal was zero-meaned. Before a computational analysis is conducted, the PPG waveforms in each data segment are visually examined and classified them into clean vs. corrupted segments. Any sort of disruption in the pulse characteristics was labeled as corrupted segments. This was done in order to later determine the accuracy of the method.

C. Computational Measures for Artifact Detection

Following the preprocessing of each PPG data segment, our approach for the detection of artifacts involves the computation of the following two parameters.

Kurtosis: Kurtosis is a statistical measure used to describe the distribution of observed data around the mean. It represents a heavy tail and peakedness or a light tail and flatness of a distribution relative to the normal distribution. The kurtosis of a normal distribution is 3. Distributions that are more outlier-prone than the normal distribution have kurtosis greater than 3; distributions that are less outlier-prone have kurtosis less than 3. The kurtosis is defined as:

$$k = \frac{E(x-\mu)^4}{\sigma^4} \quad (1)$$

Where $\mu$ is the mean of x, $\sigma$ is the standard deviation of x, and $E(t)$ represents the expected value of the quantity t.

Shannon entropy: SE quantifies how much the probability density function (PDF) of the signal is different from a uniform distribution and thus provides a quantitative measure of the uncertainty present in the signal. SE can be calculated as $$SE = -\sum_{i=1}^{k} \frac{p(i)*\log(p(i))}{\log\left(\frac{1}{k}\right)} \quad (2)$$

Where i represents the bin number, and p(i) is the probability distribution of the signal amplitude. Presently, 16 bins ($\kappa=16$) have been used to obtain a reasonably accurate measure of SE.

D. Statistical Analysis of Computational Measures:

The nonparametric Mann Whitney test was conducted on data from the involuntary motion protocol to find the significance levels ($p<0.05$) for the SE and kurtosis measures between clean vs. corrupted PPG segments. Meanwhile, the nonparametric Kruskal-Wallis test with Dunn's multiple comparison post test was conducted on data from the voluntary motion protocol to find the significance ($p<0.05$) between clean vs. noise-corrupted PPG segments for the two measures.

E. Detection of Motion/Noise Artifacts:

By varying kurtosis values from 0 to 10 with an increment of 0.1, and SE values from 0.5 to 1.0 with an increment of 0.01, receiver-operator characteristic (ROC) analysis were conducted for the population of SE and kurtosis values obtained from the respective pool of clean and corrupted PPG segments of both protocols: The substantially optimal threshold values for kurtosis and SE that produced the substantially optimal sensitivity and specificity for the detection of artifacts. (see, for example, S. H. Park et. al., Receiver Operating Characteristic (ROC) Curve: Practical Review for Radiologists, Korean J Radiol. 2004 January-March; 5(1): 11-18, which is Incorporated by reference herein is entirety for all purposes) where evaluated.

The decision rules for the detection of artifacts were formulated as follows:

$$DK_i = \begin{cases} 1 & \text{if } K_i \leq K_{Th} \\ 0 & \text{if } K_i > K_{Th} \end{cases} \quad (3)$$

where $DK_i$ refers to the decision for artifact detection based on $K_i$, kurtosis for the $i^{th}$ segment. '1' represents clean data, whereas '0' represents corrupted data. $K_{Th}$ refers to the Kurtosis threshold.

$$DS_i = \begin{cases} 1 & \text{if } SE_i \geq SE_{Th} \\ 0 & \text{if } SE_i < SE_{Th} \end{cases} \quad (4)$$

where $DS_i$ refers to the decision for artifact detection based on $SE_i$, SE for the $i^{th}$ segment. '1' represents clean data whereas '0' represents corrupted data. $SE_{Th}$ refers to the SE threshold.

The fusion of kurtosis and SE metrics with their substantially optimal threshold values for the artifact detection was further consider and the sensitivity and specificity for the fusion of these two metrics was quantified. The decision rule for the detection of artifacts using a fusion of kurtosis and SE is:

$$FD_i = \begin{cases} 1 & \text{if } DK_i + DS_i = 2 \\ 0 & \text{if } DK_i + DS_i \neq 2 \end{cases} \quad (5)$$

where $FD_i$ refers to the fusion decision for artifact detection based on both $DK_i$ and $DS_i$ for the $i^{th}$ segment. '1' represents clean data whereas '0' represents corrupted data.

Time-Frequency Spectral Analysis for the Assessment of Severity of Noise

In the second stage of this embodiment of the motion/Noise Artifact algorithm, where blood loss is being detected, how severe the noise must be to affect the dynamics of the signal in the HR frequency range is assessed (shown in FIG. 1b). Specifically, this second stage determines if some of the segments that were deemed to contain artifacts can be used for noninvasive blood loss detection, as these data may not be heavily contaminated.

This step first requires the computation of time-frequency analysis so that the amplitude modulations at each time point within the heart rate band can be obtained. This extracted amplitude modulation information is subsequently used to determine the state of usable data as detailed in the proceeding section. A time-frequency method known as the variable frequency complex demodulation method (VFCDM) to be described hereafter is used because it has been shown to provide one of the highest time-frequency resolutions.

VFCDM Analysis: The development of the VFCDM algorithm has been previously disclosed in K. H. Chon, S. Dash, and K. Ju, "Estimation of respiratory rate from photoplethysmogram data using time-frequency spectral estimation," IEEE Trans Biomed Eng, vol. 56, no. 8, pp. 2054-63, August, 2009 and in U.S. Patent Application Publication 20080287815, published on Nov. 20, 2008, corresponding to U.S. patent application Ser. No. 11/803,770, filed on May 16, 2007, both of which are incorporated by reference herein in their entirety for all purposes. Thus the VFCDM algorithm will be only briefly summarized hereinbelow.

Consider a sinusoidal signal x(t) to be a narrow band oscillation with a center frequency f0, instantaneous amplitude A(t), phase $\Phi(t)$, and the direct current component dc(t):

$$x(t) = dc(t) + A(t)\cos(2\pi f_0 t + \Phi(t)) \quad (6)$$

For a given center frequency, the instantaneous amplitude information A(t) and phase information $\Phi(t)$ can be extracted by multiplying (6) by $e^{-j2\pi f_0(t)}$, which results in the following:

$$z(t) = x(t)e^{-j2\pi f_0 t} = dc(t)e^{-j2\pi f_0 t} + \left(\frac{A(t)}{2}\right)e^{j\phi(t)} + \left(\frac{A(t)}{2}\right)e^{-j(4\pi f_0 t + \phi(t))} \quad (7)$$

A leftward shift by $e^{-j2\pi f_0(t)}$ results in moving the center frequency f0 to zero frequency in the spectrum of z(t). If z(t) in (7) is subjected to an ideal low-pass filter (LPF) with a cut-off frequency $f_c < f_0$, then the filtered signal $z_{lp}(t)$ will contain only the components of interest and the following can be extracted:

$$z_{lp}(t) = \frac{A(t)}{2}e^{j\phi(t)} \quad (8)$$

$$A(t) = 2|z_{lp}(t)| \quad (9)$$

$$\phi(t) = \tan^{-1}\frac{\text{imag}(z_{lp}(t))}{\text{real}(z_{lp}(t))} \quad (10)$$

The method can easily be extended to the variable frequency case, where the modulating frequency is expressed as $\int_0^t 2\pi f(\tau)d\tau$ and the negative exponential term used for the demodulation is $e^{-j\int_0^t 2\pi f(\tau)d\tau}$. The instantaneous frequency can be obtained using the familiar differentiation of the phase information as follows:

$$f(t) = f_0 + \frac{1}{2\pi}\frac{d\phi(t)}{d(t)} \quad (11)$$

Thus, the VFCDM method involves a two-step procedure. At first, the fixed frequency complex demodulation technique identifies the signal's dominant frequencies, shifts each dominant frequency to a center frequency, and applies a low-pass filter (LPF) to each of the center frequencies. The LPF has a cutoff frequency less than that of the original center frequency and is applied to each dominant frequency. This generates a series of band-limited signals. The instantaneous amplitude, phase and frequency information are obtained for each band-limited signal using the Hilbert transform and are combined to generate a time-frequency series (TFS). Finally, the second step of the VFCDM method is to select only the dominant frequencies and produce a high-resolution TFS.

Once the TFS of the PPG signal is obtained via the VFCDM method, the largest instantaneous amplitude at each time point within the HR band (HR±0.2 Hz) of the TFS of the VFCDM are extracted as the so-called AMHR components of the PPG that reflect the time varying amplitude modulation (AM) of the HR frequency. The initial and final 5 s of the TFS were not considered for the AMHR extraction because time frequency series have an inherent end effect that could produce false variability of the spectral power. The median value of the AMHR components was evaluated for each corrupted PPG segment.

Determination of Usable PPG Segments Corrupted with Insignificant Artifacts:

The AMHR median values were computed separately for clean PPG segments of each probe site for involuntary artifacts as well as for the voluntary artifact protocols as described above. The mean±2*SD of the AMHR median population were determined as their respective 95% statistical limits for each clean PPG data set. If the AMHR median value of the corrupted PPG segment lies within the statistical limits of the clean data, the respective corrupted PPG segment was considered as usable data; otherwise it was rejected. Thus, the model of our algorithm outlined in FIG. 1 has been designed to function in two separate stages for the detection and quantification of usable data among those that contain artifacts in PPG signals. Referring to FIG. 1a, a segment of a signal (15, FIG. 1) from PPG is preprocessed (filtered) (55, FIG. 1a), one or more indicators of volatility for the preprocessed segment are evaluated (60, FIG. 1a) to determine from comparison of the value of the one or more indicators of volatility with a predetermined threshold whether or not noise/motion artifacts are not present. If noise/motion artifacts are not present, the segment is included in calculations quantities of interest (65, FIG. 1) and the method proceeds to another segment, if another segment is available. If noise/motion artifacts are present, a time-frequency spectrum analysis is performed for the preprocessed segment and a predetermined measure of the time-frequency spectrum analysis, AMHR, is compared to a predetermined measure's threshold, the mean±2*Standard deviations (SD) of the AMHR median population of a clean sample. If the predetermined measure is within limits determined by the predetermined measure's threshold, the segment is included in calculations quantities of interest and the method proceeds to another segment, if another segment is available). If the predetermined measure is not within the limits determined by the predetermined measure's threshold, the segment is discarded and the method proceeds to another segment, if another segment is available.

Heart Rate And Heart Rate Variability Detection

In one instance, the physiological measurements are heart rate and heart rate variability. In one embodiment, the method of these teachings for obtaining measurements of heart rate and heart rate variability includes determining beats for the physiological indicator signal (examples of beat detection algorithm, these teachings not be limited to those examples, can be found in Beat Detection Algorithms, available at http://www.flipcode.com/misc/BeatDetection-Algorithms.pdf and accessed on Jan. 17, 2012), determining beat to beat intervals and applying a cubic spline algorithm to obtain a substantially continuous beat to beat interval signal indicative of heart rate.

The method for detection of beat to beat variability disclosed in United States Patent Application No. 20110166466, entitled RR INTERVAL MONITORING METHOD AND BLOOD PRESSURE CUFF UTILIZING SAME, published on Jul. 7, 2011, which is incorporated by reference herein is entirety for all purposes, could be applied. Also the methods for detection of the autonomous system imbalance disclosed in United States Patent Application 20090318983, entitled Method And Apparatus For Detection And Treatment Of Autonomic System Imbalance, published on Dec. 24, 2009, which is Incorporated by reference herein is entirety for all purposes, could be applied.

In another instance, the physiological measurement is respiratory rate. One embodiment of the method for obtaining measurements of respiratory rate includes obtaining time-frequency spectrum of the physiological indicator signal utilizing variable frequency complex demodulation (VFCDM) and obtaining respiratory rates by extracting a frequency component that has a largest amplitude for each time point at a heart rate frequency band.

An exemplary embodiment of the measurement of heart rate and heart rate variability and respiratory rate is presented hereinbelow in order to further elucidate these teachings. It should be noted that these teachings are not limited to the exemplary embodiment.

In order to compare the exemplary embodiment of the present teachings to conventional methods, experiments were performed to measure the heart rate, heart rate variability and respiratory rate using conventional techniques. Electrocardiogram (EKG) recordings were made with an HP 78354A acquisition system using the standard 5-lead electrode configuration. A respiration belt was attached around the subject's chest to monitor breathing rate (Respitrace Systems, Ambulatory Monitoring Inc.). Respiratory and EKG recordings were saved using LabChart software (ADInstruments) at a sampling rate of 400 Hz.

Data were recorded during spontaneous breathing for a single subject. Data collection was initiated as follows: (1) initiate mobile phone video recording, (2) start recordings of EKG and respiration trace 10 seconds after initiation of mobile phone recording, and (3) set mobile phone down and place subject's left index finger over camera lens. This procedure allowed for alignment of data files to within 1 second.

Metronome breathing experiments were performed on a single subject with rates set at 0.2, 0.3, and 0.4 Hz (12, 18, and 24 Beats per Minute (BPM)). The subject was asked to inhale with each beat of the metronome. Metronome recordings were made for 2 minutes for each section.

For the measurements using the exemplary embodiment of these teachings, color changes of the finger were recorded using a Motorola Droid® (Motorola Mobility, Inc.) mobile phone. The palmar side of the left index finger was placed over the camera lens with the flash turned on. Subjects were instructed to rest their finger on the camera lens without pressing down with additional force, and to keep their finger still to reduce any motion artifacts. Videos were recorded with 720×480 pixel resolution at a sampling rate of 24.99 fps in 0.3 gpp file format. The 0.3 gpp videos were converted to Audio-Video Interleave (AVI) format at 720×480 pixel resolution and 25 fps using Pazera Free 3 gp to AVI Converter 1.3 (http://www.pazera-software.com/). All further analysis was performed on the AVI videos in Matlab R2010b (The Mathworks Inc.)

For experiments assessing HR, heart rate variability (HRV), and respiration rate, only the green band from the video recordings was used. A 50×50 pixel average of a region on the video signal at each frame was made for the green band. This signal is from herein referred to as GREEN.

R-wave peak detection was performed for the EKG signal using a custom peak detection algorithm. Beats were detected for the GREEN signal using a conventional algorithm. Beat-beat intervals were computed, and cubic splined to 4 Hz to obtain the continuous HR for each signal (HREKG and HRGREEN). The power spectral density (PSD) of HR was computed using Welch periodogram method.

A section 105 of an exemplary GREEN signal obtained during spontaneous breathing is shown in FIG. 2a. The pulse signal is similar to a traditional PPG signal obtained from a pulse-oximeter. Peak detection was performed to identify the HR signal, shown in FIG. 2b along with that obtained from an EKG after R-wave peak detection. The mean±SD was 92.2±5.3 for HREKG and 92.3±5.9 for HRGREEN.

The dynamics of the HR signals-HRGREEN 110, HREKG 120 shown in FIG. 2b were assessed by frequency analysis (FIG. 2c). The dominant peak on both signals is seen to be at a low frequency<0.1 Hz. A second peak is seen on both signals in the sympathetic range (0.04-0.15 Hz), and a third peak at approximately 0.2 Hz is representative of the respiration rate. Additional high frequency components are seen in HRGREEN 112 compared to HREKG, possibly from the suboptimal low sampling frequency of the mobile phone recording.

Respiration Rate Detection

Frequency modulation (FM) and amplitude modulation (AM) sequences were extracted as described in K. H. Chon, S. Dash, and K. Ju, "Estimation of respiratory rate from photoplethysmogram data using time-frequency spectral estimation," IEEE Trans Biomed Eng, vol. 56, no. 8, pp. 2054-63, August, 2009 and in U.S. Patent Application Publication 20080287815, published on Nov. 20, 2008, corresponding to U.S. patent application Ser. No. 11/803,770, filed on May 16, 2007, both of which are incorporated by reference herein in their entirety for all purposes, and used to estimate the breathing rate (FIGS. 3a&b). Breathing rates were confirmed by taking the PSD of the respiration trace during 3 periods of metronome breathing recorded with the metronome set at 0.2, 0.3, and 0.4 Hz. Breathing rates from the respiration trace and GREEN signal using the FM sequence were estimated at the three metronome rates as 0.18 and 0.16, 0.30 and 0.32, and 0.40 and 0.38 Hz, respectively. The PSDs of the FM sequence 210, 220, 232 and respiration trace 212, 222, 230 for the three breathing rates are shown in FIG. 3c.

Oxygen Saturation Detection

In yet another instance, the physiological measurement is a measure of oxygen saturation. In one embodiment, the physiological indicator signal is acquired by placing a portion of a subject's body over an objective lens of a camera in a mobile communication device and obtaining video images of the portion of the subject's body. In that embodiment, the method of these teachings for obtaining a measure of oxygen saturation includes obtaining an average intensity of a red component and a blue component of the video images of the portion of the subject's body, the average intensity of the red component and the average intensity of the blue component constituting DCRED and DCBLUE respectively, obtaining a standard deviation of the red component and the blue component, the standard deviation of the red component and the blue component constituting ACRED and ACBLUE respectively, and obtaining the measure of oxygen saturation (SpO2) by $$SpO2 = A - B\frac{\frac{AC_{RED}}{DC_{RED}}}{\frac{AC_{BLUE}}{DC_{BLUE}}}.$$

An exemplary embodiment of the measure of oxygen saturation is presented hereinbelow in order to further elucidate these teachings. It should be noted that these teachings are not limited to the exemplary embodiment.

In order to compare the exemplary embodiment of the present teachings to conventional methods, experiments were performed to measure oxygen saturation.

Breath holding experiments were performed to assess the impact of reduced oxygen saturation on the optical recordings on two subjects. A commercial reflectance pulse-oximeter (Radical SETTM, Masimo) was placed on the left ring finger to record 1 sec measurements of SpO2. The mobile phone camera lens was placed underneath the subjects' left index fingertip. A black cloth was placed around the finger on the camera lens to isolate the sensor from light emanating from the commercial pulse-oximeter. The data files were aligned by starting the data logging of the pulse-oximeter by verbal command after the mobile phone recording started, and using the audio file to determine the initiation time point.

Subjects were asked to breathe normally for approximately 30 seconds, exhale, and then to hold their breath till they felt discomfort. Two consecutive breath holding periods were recorded for each subject.

Oxygen Saturation Monitoring

The ratio of RED and BLUE in the equation for SpO provided hereinabove was computed and the A and B parameters were estimated for each subject using the commercial pulse-oximeter SpO2 values as a reference. For the subject shown in FIG. 4a, A and B in $$SpO2 = A - B\frac{\frac{AC_{RED}}{DC_{RED}}}{\frac{AC_{BLUE}}{DC_{BLUE}}}$$

and B in were determined to be 154.5 and 220.3, respectively, and for the subject in FIG. 4b, A and B were determined to be 155.7 and 265.5. (In FIGS. 4a and 4b, measurements from the pulse oxymeter are labeled 310, 312, while measurements from these teachings are labeled 320, 322. It can be observed in FIGS. 4a, 4b that $SpO_2$ decreases monitored with the commercial pulse-oximeter appear to cause decreases in our computed $SpO_2$ value obtained from the mobile phone recording. For the subject in FIG. 4a, a minimum $SpO_2$ level of 84% was recorded from the commercial pulse-oximeter and a minimum of 81% was computed with $$SpO2 = A - B\frac{\frac{AC_{RED}}{DC_{RED}}}{\frac{AC_{BLUE}}{DC_{BLUE}}}.$$

It should be noted that, although offline analysis we performed in the above exemplary embodiments, given the current processing power available in mobile phones (currently 1 GHz dual-core processors available), performing the analysis directly on a mobile phone is within the scope of these teachings.

Blood Loss Detection

In a further instance, the physiological measurement is a measure of blood loss. One embodiment of the method for obtaining a measure of blood loss includes obtaining time-frequency spectrum of the physiological indicator signal utilizing variable frequency complex demodulation (VFCDM), obtaining the amplitude modulation (AM) series from a set of the largest instantaneous amplitude at each time sample within the heart rate frequency band of the time-frequency spectrum and determining whether the amplitude modulation decreases, a decrease in the amplitude modulation indicating blood volume loss in the subject.

An exemplary embodiment of the method for obtaining a measure of blood loss is disclosed in U.S. Provisional Application Ser. No. 61/434,856, filed Jan. 21, 2011, entitled, SYSTEM AND METHOD FOR THE DETECTION OF BLOOD VOLUME LOSS" and in Nandakumar Selvaraj, Christopher G. Scully, Kirk H. Shelley, David G. Silverman, and Ki H. Chon, Early Detection of Spontaneous Blood Loss using Amplitude Modulation of Photoplethysmogram, 33rd Annual International Conference of the IEEE EMBS Boston, Mass. USA, August 30-Sep. 3, 2011, both of which are incorporated by reference herein in their entirety for all purposes.

Other embodiments of the method for obtaining a measure of blood loss are disclosed in WIPO International Publication No. WO 2011/050066 A2, entitled "Apparatus And Method For Respiratory Rate Detection And Early Detection Of Blood Loss Volume," published on Apr. 28, 2011, which is incorporated by reference herein in its entirety for all purposes.

Atrial Fibrillation Detection

In a further instance, the physiological measurement is a measure of atrial fibrillation. One embodiment of the method for obtaining a measure of atrial fibrillation includes obtaining a time-varying coherence function by multiplying two time-varying transfer functions (TVFTs), the two time-varying transfer functions obtained using two adjacent data segments with one data segment as input signal and the other data segment as output to produce the first TVTF, the second TVTF is produced by reversing the input and output signals and determining whether the time-varying coherence function (TVCF) is less than a predetermined quantity. In another embodiment, determining whether the time-varying coherence function is less than the predetermined quantity includes obtaining one or more indicators of atrial fibrillation and determining whether the one or more indicators of atrial fibrillation exceed predetermined thresholds. In one instance, the one or more indicators of atrial fibrillation include a variance of the time-varying coherence function. In another instance, the one or more indicators of atrial fibrillation also include Shannon entropy. In yet another instance, the predetermined thresholds are determined using receiver operator characteristic (ROC) analysis.

In the embodiment of the method for obtaining a measure of atrial fibrillation disclosed hereinabove, the TVCF is estimated by the multiplication of two time-varying transfer functions (TVTFs). The two TVTFs are obtained using two adjacent data segments with one data segment as the input signal and the other data segment as the output to produce the first TVTF; the second TVTF is produced by reversing the input and output signals. It has been found that the resultant TVCF between two adjacent normal sinus rhythm segments show high coherence values (near 1) throughout the entire frequency range. However, if either or both segments partially or fully contain AF, the resultant TVCF is significantly lower than 1. When TVCF was combined with Shannon entropy (SE), even more accurate AF detection rate of 97.9% are obtained for the MIT-BIH Atrial Fibrillation (AF) database (n=23) with 128 beat segments.

In the embodiment disclosed herein above, the TVCF is obtained by the multiplication of the two time-varying transfer functions. To demonstrate the use of the TVTF in obtaining the TVCF, the TVCF is first defined via the nonparametric time-frequency spectra as $$|\gamma(t,f)|^4 = \frac{|S_{xy}(t,f)|^2}{S_{xx}(t,f)S_{yy}(t,f)} \frac{|S_{yx}(t,f)|^2}{S_{yy}(t,f)S_{xx}(t,f)} \quad (12)$$

where $S_{xy}(t,f)$ and $S_{xy}(t,f)$ represent the time-frequency cross-spectrum, and $S_{xx}(t,f)$ and $S_{yy}(t,f)$ represent the auto spectra of the two signals x and y, respectively. Specifically, the first term in Eq. (12) is the coherence function when x is considered as the input and y as the output. Similarly, the second term in Eq. (12) is the coherence function when y is considered as the input and x as the output. For a linear time varying (TV) system with x as the input and y as the output, the TVTF in terms of time-frequency spectra can be obtained as $$H_{x \to y}(t,f) = \frac{S_{xy}(t,f)}{S_{xx}(t,f)} \quad (13)$$

where $H_{x \to y}(t,f)$ is the TVTF from the input x to the output y signal. Similarly, for a linear TV system with y as the input and x as the output, the TVTF can be obtained as $$H_{y \to x}(t,f) = \frac{S_{yx}(t,f)}{S_{yy}(t,f)} \quad (14)$$

Thus, the time-varying magnitude $|\gamma(t,f)|^2$ is obtained by multiplying the two transfer functions, $$|H_{x \to y}(t,f) \cdot H_{y \to x}(t,f)|. \quad (15)$$

Given the relationship of (15), a high resolution TVCF can be obtained from ARMA models:

$$y(n) = -\sum_{i=1}^{P_2} a(n,i)y(n-i) + \sum_{j=0}^{Q_2} b(n,j)x(n-j) \quad (16\text{-}1)$$

$$x(n) = -\sum_{i=1}^{P_2} \alpha(n,i)x(n-i) + \sum_{j=0}^{Q_2} \beta(n,j)y(n-j) \quad (16\text{-}2)$$

where (16-1) represents y(n) as the output and x(n) as the input. Similarly, (16-2) represents x(n) as the output and y(n) as the input. Given the ARMA models of (16), the two transfer functions of (15) can be obtained as $$H_{x \to y}(n, e^{jw}) = \frac{B(n, e^{jw})}{A(n, e^{jw})} = \frac{\sum_{i=0}^{Q_1} b(n,j)e^{-jwi}}{1 + \sum_{i=1}^{P_1} a(n,i)e^{-jwi}} \quad (17)$$

$$H_{y \to x}(n, e^{jw}) = \frac{\beta(n, e^{jw})}{\alpha(n, e^{jw})} = \frac{\sum_{i=0}^{Q_2} \beta(n,j)e^{-jwi}}{1 + \sum_{i=1}^{P_2} a(n,i)e^{-jwi}}$$

Finally, the TVCF can be obtained by multiplying the two transfer functions as described in (17). For the parameter estimation, the time-varying optimal parameter search (TVOPS) criterion can be used, which has been shown to be accurate when applied to many diverse physiological signals. For the physiological signals considered, the TVOPS has been shown to be more accurate than the AIC, minimum description length (MDL) and the fast orthogonal search criterion. For TVOPS, time-varying coefficients are expanded onto a set of basis functions. It has been previously demonstrated that Legendre polynomials are a good choice for capturing dynamics that are smoothly changing with time.

AF Detection: Variance of TVCF

For AF detection, two adjacent beat segments with the length denoted as seg has been formulated using the following ARMA models:

$$S_{i+1:i+seg}(n) = \quad (18)$$

$$-\sum_{i=1}^{P_2} a(n,i)S_{i+1:i+seg}(n-i) + \sum_{j=0}^{Q_2} b(n,j)S_{i+seg+1:i+2seg}(n-j)$$

-continued $$S_{i+seg+1:i+2 \cdot seg}(n) =$$
$$-\sum_{i=1}^{P_2} \alpha(n,i) S_{i+seg+1:i+2 \cdot seg}(n-i) + \sum_{j=0}^{Q_2} \beta(n,j) S_{i+1:i+seg}(n-j)$$

where $S_{i+1:i+seg}(n)$ and $S_{i+seg+1:i+2seg}(n)$ are two adjacent RR interval time series from the $(i+1)^{th}$ to the $(i+seg)^{th}$ and from the $(i+seg+1)^{th}$ to the $(i+2 \cdot seg)^{th}$, respectively. By substituting (18) into (17), the two transfer functions are obtained, and the TVCF is obtained by multiplication of the two TVCFs.

An exemplary embodiment of the measure of atrial fibrillation is presented hereinbelow in order to further elucidate these teachings. It should be noted that these teachings are not limited to the exemplary embodiment.

The detection algorithm was tested on four databases using 128 beat segments: the MIT-BIH AF database, the MIT-BIH normal sinus rhythm (NSR) database (n=18), the MIT-BIH Arrhythmia database (n=48), and a clinical 24-hour Holter AF database (n=15).

Figure 5:
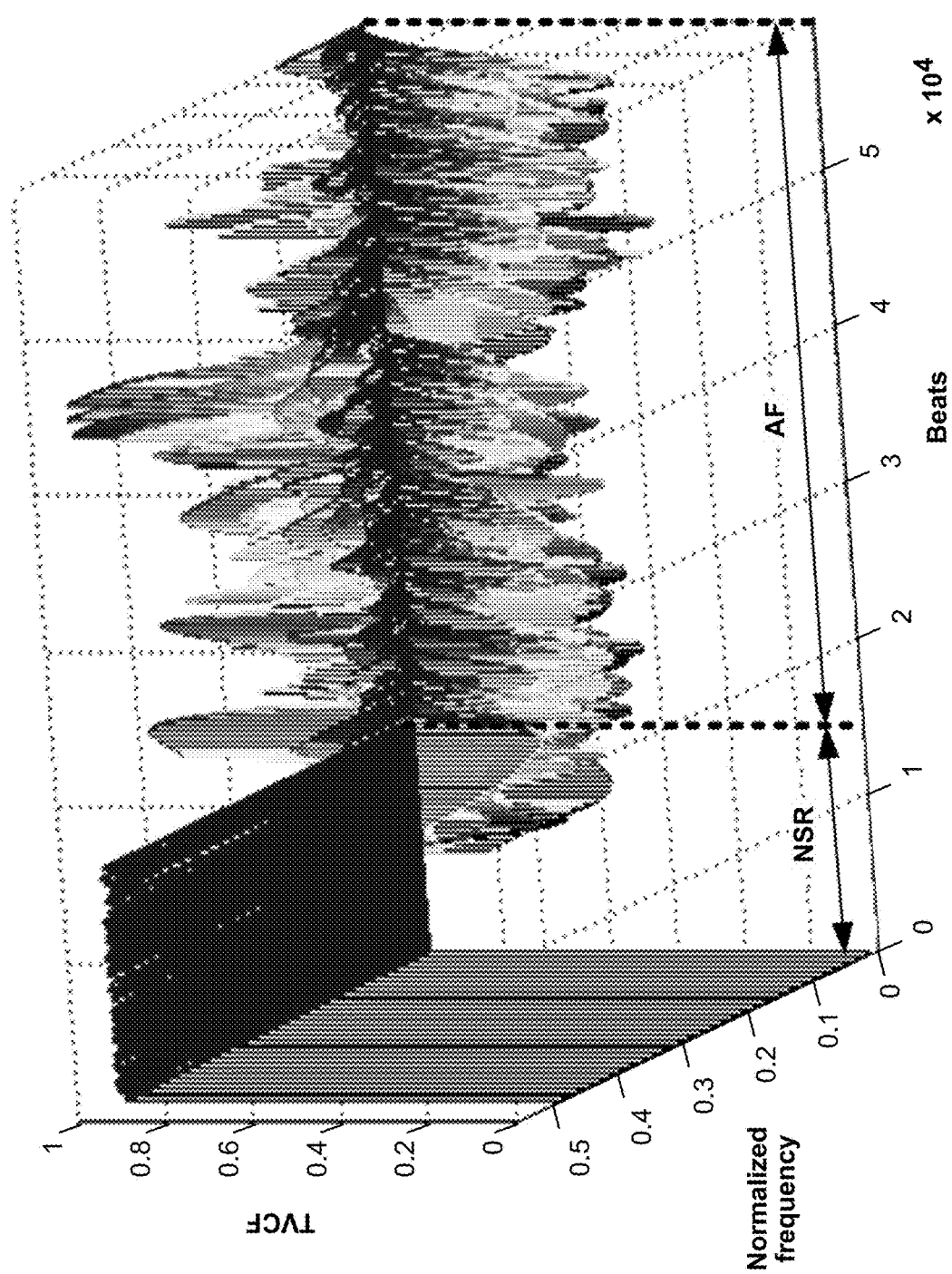
FIG. 5 illustrates a schematic graphical representation of a resultant Time-Varying Coherence Function (TVCF) in a further exemplary embodiment of the method of these teachings.

In order to illustrate AF detection, the TVCF are calculated using ARMA (P1=5,Q1=5) with the first order Legendre function for subject 8455 of the MIT-BIH AF database. The first order of Legendre polynomials was used as this choice resulted in the best accuracy for the MIT-BIH AF database (N=23). The optimal ARMA model order was found to be P1=5 and Q1=5 with seg=128, which will be explained in detail in the proceeding section. A 128 beat segment was used which was then shifted by 128 beats. A 64 point FFT was used, which resulted in a frequency resolution of 0.0156 Hz. FIG. 5 shows the resultant TVCFs according to each beat and normalized frequency (assuming a Nyquist frequency of 0.5 Hz). As shown in FIG. 5, the TVCF values are close to one throughout the entire frequency range for the two adjacent normal sinus rhythm (NSR) data segments. However, the TVCF values significantly decreased when either or both segments partially or fully contained AF.

Figures 6A, 6B:
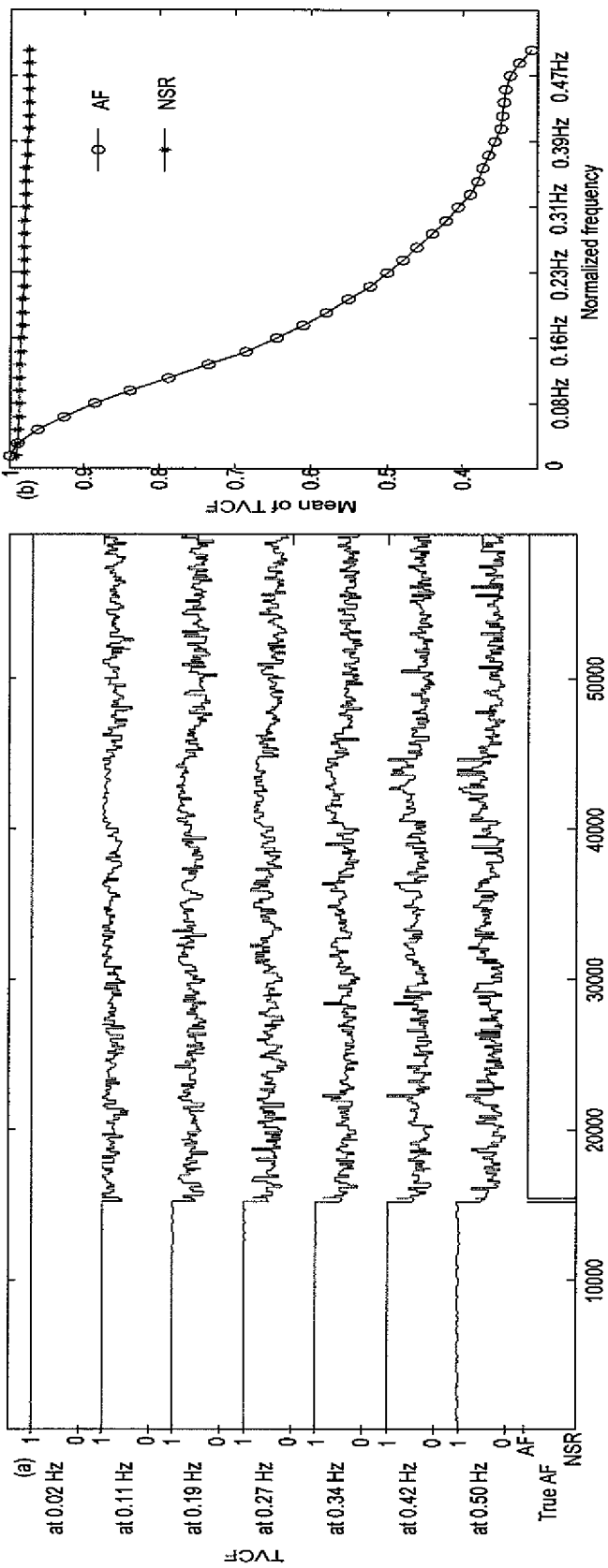
FIGS. 6a and 6b are schematic graphical representations of the TVCF at different frequencies in the further exemplary embodiment of the method of these teachings.

As shown in FIG. 5, it is observed that the TVCF values are highly varying for different frequencies when the patient is in AF. That is, high frequencies tend to have lower coherence values than lower frequencies, in AF (see FIGS. 6a, 6b). To illustrate this phenomenon in more detail, some of the TVCF values are shown selected at various frequencies from FIG. 5 as a function of time in FIG. 6(a). FIG. 6(b) shows the corresponding average values of TVCF according to each normalized frequency and each 128-beat segment for both the AF and NSR databases. It is noted that for AF data, TVCF values start close to one at low frequencies but they drop to low values quickly as the frequency increases. However, for NSR data, the TVCFs are nearly constant (slightly decreasing) at near unit values for all frequencies. This can be explained by the fact that the selected ARMA model terms for AF include largely self and its delay of one lag terms (e.g. x(n), x(n−1), y(n) and y(n−1)), as expected, thus, TVCF values will be high only at the low frequencies and become lower as frequencies increase. Also note in the left panel of FIG. 6, it is observed that the variance of TVCF values is significantly high for AF but nearly constant for NSR.

Based on the latter observation as described above, AF detection is performed by examining the variance of TVCF through the entire frequency range. For each beat, the variance of TVCF values, termed the frequency variations (FV), is calculated among all frequencies. Using FV-TVCF, the AF detection performance was investigated on the entire MIT-BIH AF database.

Referring now to FIGS. 7A and 3B, FV-TVCF values and true AF annotation for three representative subjects 4048, 735 and 7162 of the MIT-BIH AF database are shown. In FIG. 7(a), the data set 4048 contains seven AF episodes with lengths of 206, 66, 37, 34, 388, 40 and 42 beats, and the values of FV-TVCF increase in the beats where AF occurs. In FIG. 7(b), the data set 735 contains one AF episode with a length of 332 beats whereas for the dataset 7162, AF episodes persist for the entire time segment shown. The FV-TVCF values reflect this by never returning to a value of zero.

Ectopic Beat Elimination and Shannon Entropy Combination

A NSR segment including premature or ectopic beats may also result in lower TVCF values. In order to reduce the effect of the premature and ectopic beats, we eliminated outliers and filtered ectopic beats. To summarize, premature or ectopic beats can be recognized by their signature short-long RR sequence between normal RR intervals. For each RR interval in the time series, the ratio RR(i)/RR(i−1) was computed, where RR(i) is the ith beat, and eliminated RR(i) and RR(i+1) when the following three conditions were satisfied: 1) RR(i)/RR(i−1)<perc1, 2) RR(i+1)/RR(i)>perc99 and 3) RR(i+1)/RR(i+2)×perc25, where perc1, perc25 and perc99 are the 1st, 25th and 99th percentiles based on a histogram of the RR interval values, respectively.

Shannon entropy (SE) as in (19) was also combined with FV-TVCF, to increase the accuracy of AF detection. SE has been shown to be a robust detector of AF and is estimated according to the following calculation:

$$SE = -\sum_{u=1}^{N_{bin}} p(u) \frac{\log(p(u))}{\log\left(\frac{1}{N_{bin}}\right)} \qquad (19)$$

Note that $N_{bin}$ was selected for the best accuracy according to segment lengths while $N_{bin}=16$ was selected.

Detector Optimization

In one embodiment, the condition for AF detection can be given by a simple logical AND condition:

If (FV≥$TH_{var}$) AND (SE≥$TH_{SE}$), then classify it as AF.
Else classify it as non-AF.

$TH_{var}$ and $TH_{SE}$ are the threshold values of the variance and the Shannon entropy, respectively, and are selected based on the best accuracy; specifically, we used receiver operator characteristic (ROC) analyses. For each combination of $TH_{var}$ and $TH_{SE}$, the number of True Positives (TP), True Negatives (TN), False Positives (FP) and False Negatives (FN) were found, and used the accuracy (TP+TN)/(TP+TN+FP+FN) on the MIT-BIH AF database. In addition, the sensitivity TP/(TP+FN) and specificity TN/(TN+FP) were calculated. The procedure was repeated by changing the order of ARMA model and the lengths of segments. Note that the ARMA model order was restricted by setting P1=Q1. After finding the values of $TH_{var}$ and $TH_{SE}$ with each different number of model orders and lengths of segments, the same parameters were applied to the databases from MIT-BIH and the clinical AF database.

In another embodiment of the method for obtaining a measure of atrial fibrillation, the method, using the Root Mean Square of Successive Differences (RMSSD), disclosed in United States Patent Application No. 20110166466, entitled RR INTERVAL MONITORING METHOD AND BLOOD PRESSURE CUFF UTILIZING SAME, published on Jul. 7, 2011, which is incorporated by reference herein is entirety for all purposes, is applied.

In one or more embodiments, the system of these teachings for physiological parameter monitoring includes a physiological indicator signal sensing component (sensor) and a mobile communication device having an analysis component analyzing the physiological indicator signal to obtain measurements of one or more physiological parameters and a motion artifact detection component detecting effects of motion artifacts in the measurements of the one or more physiological parameters.

In one instance, the mobile communication device includes one or more processors and one or more computer usable media, where the computer usable media has computer readable code embodied therein that causes the processor to analyze the physiological indicator signal to obtain measurements of one or more physiological parameters and to detect effects of motion artifacts in the measurements of the one or more physiological parameters. In one or more embodiments, the computer readable code causes the processor to implement the methods described hereinabove.

It should be noted that other embodiments of the mobile communication device, such as the use of ASICs or FPGAs in order to implement the analysis component and/or the motion artifact detection component are within the scope of these teachings.

Figure 8:
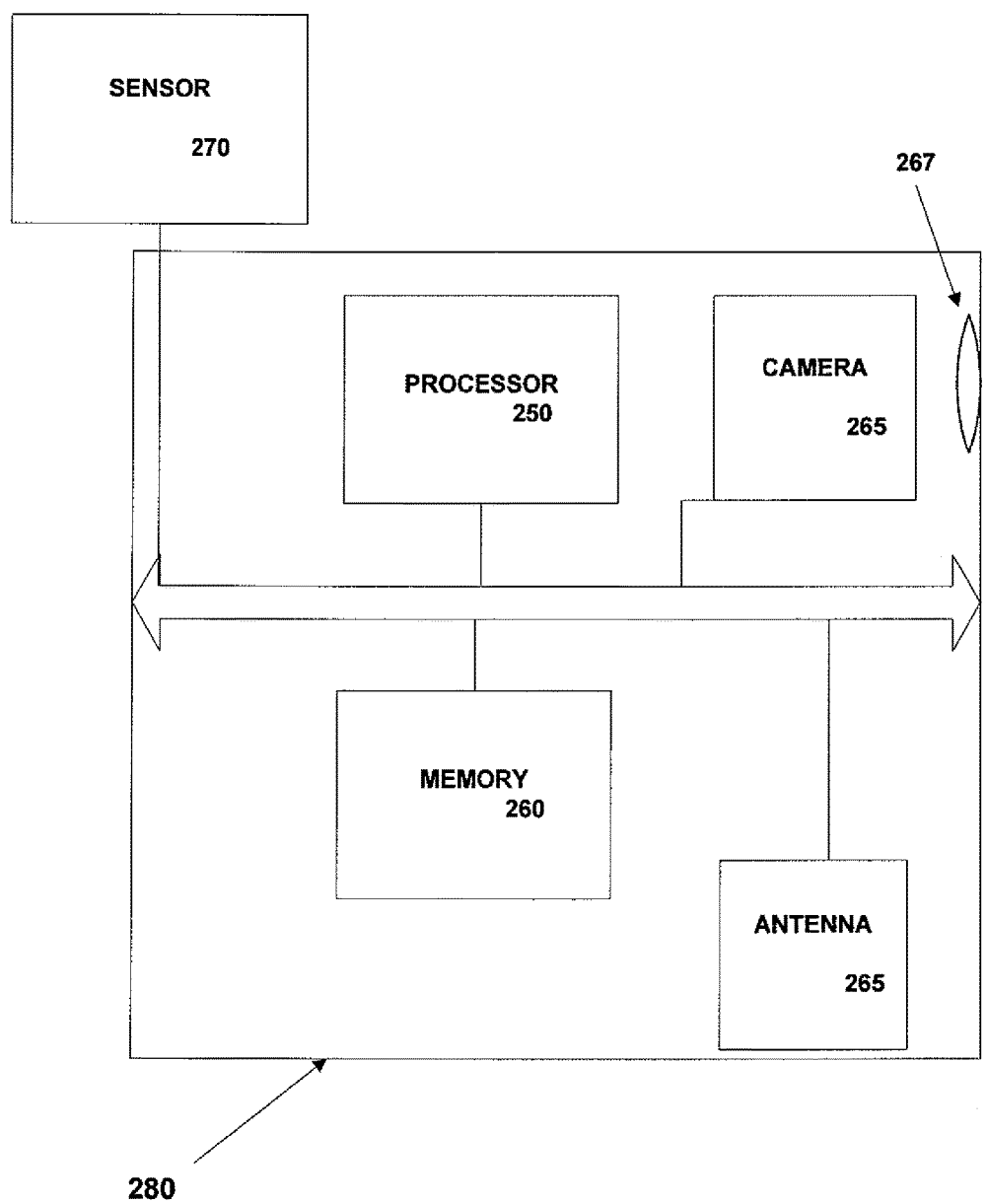
FIG. 8 represents a schematic block diagram representation of one embodiment of the system of these teachings.

FIG. 8 is a block diagram representation of one embodiment of the system of these teachings. Referring to FIG. 8, in the embodiment shown therein, a mobile communication system 280 includes a processor 250 and one or more memories 260. A physiological indicator signal sensing component (sensor) 270 supplies a physiological indicators signal to the mobile communication device 280. The sensor 270 can be a photoplethysmographic (PPG) sensor or an electrocardiogram (EKG) sensor. In the embodiment shown in FIG. 8, a camera 265, where the camera as an objective lens 267, can also supply the physiological indicators signal to the mobile communication device 280. The one or more memories 260 have computer usable code embodied therein that causes the processor 250 to that causes the processor to analyze the physiological indicator signal to obtain measurements of one or more physiological parameters and to detect effects of motion artifacts in the measurements of the one or more physiological parameters. In one or more instances, the computer readable code causes the processor 250 to perform the implement the methods described hereinabove.

The one or more memories 260 represent one embodiment of computer usable media having computer readable code embodied therein that causes a processor to implement the methods of these teachings. Embodiments of the method of these teachings are described hereinabove and the computer readable code can cause a processor to implement those embodiments.

In the embodiment shown in FIG. 8, the mobile communication device 280 also includes an antenna 265 that enables communications through one or more of a variety of wireless protocols or over wireless networks. It should be noted that, although the sensor 270 is shown as being directly connected to the mobile communication device 280, embodiments in which the sensor 270 provides the physiological indicators signal to the mobile communication device 280 through a wireless connection are also within the scope of these teachings.

For the purposes of describing and defining the present teachings, it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Elements and components described herein may be further divided into additional components or joined together to form fewer components for performing the same functions.

Each computer program may be implemented in any programming language, such as assembly language, machine language, a high-level procedural programming language, or an object-oriented programming language. The programming language may be a compiled or interpreted programming language.

Each computer program may be implemented in a computer program product tangibly embodied in a computer-readable storage device for execution by a computer processor. Method steps of the invention may be performed by a computer processor executing a program tangibly embodied on a computer-readable medium to perform functions of the invention by operating on input and generating output.

Common forms of computer-readable media include, for example, a floppy disk, a flexible disk, hard disk, magnetic tape, or any other magnetic medium, a CDROM, any other optical medium, any physical medium with patterns of holes, a RAM, a PROM, and EPROM, a FLASH-EPROM, any other memory chip or cartridge, all of which are non-transitory. As stated in the USPTO 2005 Interim Guidelines for Examination of Patent Applications for Patent Subject Matter Eligibility, 1300 Off. Gaz. Pat. Office 142 (Nov. 22, 2005), "On the other hand, from a technological standpoint, a signal encoded with functional descriptive material is similar to a computer-readable memory encoded with functional descriptive material, in that they both create a functional interrelationship with a computer. In other words, a computer is able to execute the encoded functions, regardless of whether the format is a disk or a signal."

Although the invention has been described with respect to various embodiments, it should be realized these teachings are also capable of a wide variety of further and other embodiments within the spirit and scope of the appended claims.

What is claimed is:

1. A method for physiological parameter monitoring, the method comprising:
   providing a physiological indicator signal to a handheld mobile communication device; the physiological indicator signal being obtained from one of an image acquisition component, a photoplethysmographic (PPG) sensor and an electrocardiogram sensor;
   analyzing, using the handheld mobile communication device, the physiological indicator signal;
   obtaining, from said analyzing, measurements of one or more physiological parameters; and
   detecting, using the handheld mobile communication device and using only the measurements of one or more physiological parameters, effects of motion artifacts in the measurements of the one or more physiological parameters and deciding whether to retain the measurements based on detected effects of motion artifacts;
   wherein detecting effects of motion artifacts in the measurements comprises:

a. bandpass filtering and detrending a segment from the measurement of one physiological parameter; wherein a bandpass filtered and detrended segment is hereinafter referred to as a preprocessed segment;
b. obtaining a value of at least one indicator of volatility, used in determining whether motion artifacts are present, for the preprocessed segment; the at least one indicator of volatility being at least Shannon entropy (SE) for the preprocessed segment; where $$SE = -\sum_{i=1}^{k} \frac{p(i) * \log(p(i))}{\log\left(\frac{1}{k}\right)}$$

and where i represents the bin number and, p(i) is the probability distribution of the preprocessed segment;
c. including the segment in analyses of physiological measurements, when comparison of the value of the at least one indicator of volatility with a predetermined threshold indicates noise/motion artifacts are not present; and
d. selecting another segment of the signal from the physiological measurement and proceeding to step (a) when the value of the at least one indicator of volatility is less than a predetermined threshold and when another segment is available.

2. The method of claim 1 wherein said at least one indicator of volatility also comprises kurtosis.

3. The method of claim 1 wherein the predetermined threshold is determined using receiver operator characteristic (ROC) analysis.

4. The method of claim 1 wherein providing a physiological indicator signal comprises:
placing a portion of a subject's body over an objective lens of a camera in a handheld mobile communication device; and
obtaining video images of the portion of the subject's body.

5. The method of claim 1 wherein providing a physiological indicator signal comprises obtaining a signal from a physiological monitoring sensor.

6. The method of claim 5 wherein the physiological monitoring sensor is a photoplethysmographic (PPG) sensor or an electrocardiogram sensor.

7. The method of claim 1 wherein the one or more physiological measurements comprise heart rate and heart rate variability.

8. The method of claim 1 wherein obtaining measurements of heart rate and heart rate variability comprise:
determining beats for the physiological indicator signal;
determining beat to beat intervals; and
applying a cubic spline algorithm to obtain a substantially continuous beat to beat interval signal indicative of heart rate.

9. The method of claim 1 wherein the one or more physiological measurements comprise respiratory rate.

10. The method of claim 9 wherein measurement of respiratory rate comprises:
obtaining time-frequency spectrum of the physiological indicator signal utilizing variable frequency complex demodulation (VFCDM); and
obtaining respiratory rates by extracting a frequency component that has a largest amplitude for each time point at a heart rate frequency band.

11. The method of claim 1 wherein the one or more physiological measurements comprise a measure of oxygen saturation.

12. The method of claim 11 wherein providing a physiological indicator signal comprises:
placing a portion of a subject's body over an objective lens of a camera in a mobile communication device; and
obtaining video images of the portion of the subject's body,
wherein obtaining the measure of oxygen saturation comprises:
obtaining an average intensity of a red component and a blue component of the video images of the portion of the subject's body; the average intensity of the red component and the average intensity of the blue component constituting $DC_{RED}$ and $DC_{BLUE}$ respectively;
obtaining a standard deviation of the red component and the blue component; the standard deviation of the red component and the blue component constituting $AC_{RED}$ and $AC_{BLUE}$ respectively; and
obtaining the measure of oxygen saturation (SpO2) by $$SpO2 = A - B\frac{\frac{AC_{RED}}{DC_{RED}}}{\frac{AC_{BLUE}}{DC_{BLUE}}}.$$

13. The method of claim 1 wherein the one or more physiological measurements comprise a measure of blood loss.

14. The method of claim 13 wherein obtaining the measure of blood loss comprises:
obtaining time-frequency spectrum of the physiological indicator signal utilizing variable frequency complex demodulation (VFCDM);
obtaining the amplitude modulation (AM) series from a set of the largest instantaneous amplitude at each time sample within the heart rate frequency band of the time-frequency spectrum; and
determining whether the amplitude modulation decreases; a decrease in the amplitude modulation indicating blood volume loss in subject.

15. The method of claim 1 wherein the one or more physiological measurements comprise a measure of atrial fibrillation.

16. A method for physiological parameter monitoring, the method comprising:
providing a physiological indicator signal to a handheld mobile communication device; the physiological indicator signal being obtained from one of an image acquisition component, a photoplethysmographic (PPG) sensor and an electrocardiogram sensor;
analyzing, using the handheld mobile communication device, the physiological indicator signal; wherein analysis does not include Independent Component Analysis;
obtaining, from said analyzing, measurements of one or more physiological parameters; and
detecting, using the handheld mobile communication device and using only the measurements of one or more physiological parameters, effects of motion artifacts in the measurements of the one or more physiological parameters and deciding whether to retain the measurements based on effects of motion artifacts in the measurements;
wherein the one or more physiological measurements comprise a measure of atrial fibrillation;
wherein obtaining the measure of atrial fibrillation comprises:
obtaining a time-varying coherence function by multiplying two time-varying transfer functions (TVFTs), the two time-varying transfer functions obtained using two adjacent data segments, from the physiological indicator signal, one of the two adjacent data segment as an input signal and another of the two adjacent data segment as an output signal to produce a first TVTF; a second TVTF is produced by reversing the input and the output signals, using said another of the two adjacent data segment as the input signal and said one of the two adjacent data segment as the output signal; and
determining whether the time-varying coherence function is less than a predetermined quantity.

17. The method of claim 16 wherein determining whether the time-varying coherence function is less than the predetermined quantity comprises:
obtaining one or more indicators of atrial fibrillation; and
determining whether the one or more indicators of atrial fibrillation exceed predetermined thresholds.

18. The method of claim 17 wherein the one or more indicators of atrial fibrillation comprise a variance of the time-varying coherence function.

19. The method of claim 18 wherein the one or more indicators of atrial fibrillation also comprise Shannon entropy.

20. The method of claim 17 wherein the predetermined thresholds are determined using receiver operator characteristic (ROC) analysis.

21. A system for physiological parameter monitoring, the system comprising:
a physiological indicator signal sensing component; the physiological indicator signal sensing component being one of an image acquisition component, a photoplethysmographic (PPG) sensor and an electrocardiogram sensor; and a handheld mobile communication device comprising:
at least one processor; and
at least one computer usable medium, the computer usable medium having computer readable code embodied therein, the computer readable code causing the at least one processor to:
analyze the physiological indicator signal;
obtain, from results of analyzing, measurements of one or more physiological parameters; and
detect effects of motion artifacts in the measurements of the one or more physiological parameters;
wherein the computer readable code, in causing the at least one processor to detect effects of motion artifacts, causes the at least one processor to:
a. bandpass filter and detrend a segment from the measurement of one physiological parameter; wherein a bandpass filtered and detrended segment is hereinafter referred to as a preprocessed segment;
b. obtain a value of at least one indicator of volatility, used in determining whether motion artifacts are present, for the preprocessed segment; the at least one indicator of volatility being at least Shannon entropy (SE) for the preprocessed segment; where $$SE = -\sum_{i=1}^{k} \frac{p(i)*\log(p(i))}{\log\left(\frac{1}{k}\right)}$$

and where i represents the bin number, and p(i) is the probability distribution of the preprocessed segment;
c. include the segment in analyses of physiological measurements when comparison of the value of the at least one indicator of volatility with a predetermined threshold indicates noise/motion artifacts are not present; and
d. select another segment of the signal from the physiological measurement and proceeding to step (a) when the value of the at least one indicator of volatility is less than a predetermined threshold and another segment is available.

22. The system of claim 21 wherein said at least one indicator of volatility also comprises kurtosis.

23. The system of claim 21 wherein the predetermined threshold is determined using receiver operator characteristic (ROC) analysis.

24. The system of claim 21 wherein the physiological indicator signal sensing component comprises an image acquisition component, said acquisition component capable of acquiring a number of frames, each frame acquired at a predetermined time.

25. The system of claim 24 wherein the handheld mobile communications device comprises said image acquisition component.

26. The system of claim 21 wherein the physiological indicator signal sensing component comprises a physiological monitoring sensor.

27. The system of claim 26 wherein the physiological monitoring sensor is a photoplethysmographic (PPG) sensor or an electrocardiogram sensor.

28. The system of claim 21 wherein the physiological indicator signal sensing component comprises an image acquisition component, said acquisition component capable of acquiring a number of frames, each frame acquired at a predetermined time; wherein said image acquisition component acquires a color image having red, green and blue components; wherein one or more physiological measurements comprise a measure of oxygen saturation; and wherein the computer readable code, in causing the at least one processor to analyze the physiological indicator signal, causes the at least one processor to:
obtain an average intensity of a red component and a blue component of the images of a portion of a subject's body; the average intensity of the red component and the average intensity of the blue component constituting $DC_{RED}$ and $DC_{BLUE}$ respectively;
obtain a standard deviation of the red component and the blue component; the standard deviation of the red component and the blue component constituting ACRED and ACBLUE respectively; and
obtain the measure of oxygen saturation by $$SpO2 = A - B\frac{\frac{AC_{RED}}{DC_{RED}}}{\frac{AC_{BLUE}}{DC_{BLUE}}}.$$

29. The system of claim 21 wherein the one or more physiological measurements comprise heart rate and heart rate variability; and wherein the computer readable code, in causing the at least one processor to analyze the physiological indicator signal, causes the at least one processor to:
  determine beats for the physiological indicator signal;
  determine beat to beat intervals; and
  apply a cubic spline algorithm to obtain a substantially continuous beat to beat interval signal indicative of heart rate.

30. The system of claim 21 wherein the one or more physiological measurements comprise respiratory rate; and wherein the computer readable code, in causing the at least one processor to analyze the physiological indicator signal, causes the at least one processor to:
  obtain time-frequency spectrum of the physiological indicator signal utilizing variable frequency complex demodulation (VFCDM); and
  obtain respiratory rates by extracting a frequency component that has a largest amplitude for each time point at a heart rate frequency band.

31. The system of claim 21 wherein the one or more physiological measurements comprise a measure of blood loss; and wherein the computer readable code, in causing the at least one processor to analyze the physiological indicator signal, causes the at least one processor to:
  obtain time-frequency spectrum of the physiological indicator signal utilizing variable frequency complex demodulation (VFCDM);
  obtain the amplitude modulation (AM) series from set of the largest instantaneous amplitude at each time sample within the heart rate frequency band of the time-frequency spectrum; and
  determine whether the amplitude modulation decreases; a decrease in the amplitude modulation indicating blood volume loss in subject.

32. A system for physiological parameter monitoring, the system comprising:
  a physiological indicator signal sensing component; and a handheld mobile communication device comprising:
  at least one processor; and
  at least one computer usable medium, the computer usable medium having computer readable code embodied therein, the computer readable code causing the at least one processor to:
  analyze the physiological indicator signal; the physiological indicator signal being obtained from one of an image acquisition component, a photoplethysmographic (PPG) sensor and an electrocardiogram sensor;
  wherein analysis does not include Independent Component Analysis;
  obtain, from results of analyzing, measurements of one or more physiological parameters; and
  detect effects of motion artifacts, using only the measurements of one or more physiological parameters, in the measurements of the one or more physiological parameters; wherein the one or more physiological measurements comprise a measure of atrial fibrillation; and wherein the computer readable code, in causing the at least one processor to analyze the physiological indicator signal, causes the at least one processor to:
  obtain a time-varying coherence function by multiplying two time-varying transfer functions (TVFTs), the two time-varying transfer functions obtained using two adjacent data segments from the physiological indicator signal, one of the two adjacent data segment as an input signal and another of the two adjacent data segment as an output signal to produce a first TVTF; a second TVTF is produced by reversing the input and the output signals, using said another of the two adjacent data segment as the input signal and said one of the two adjacent data segment as the output signal; and
  determine whether the time-varying coherence function is less than a predetermined quantity.

33. The system of claim 32 wherein the computer readable code, in causing the at least one processor to determine whether the time-varying coherence function is less than the predetermined quantity, causes the at least one processor to:
  obtain one or more indicators of atrial fibrillation; and
  determine whether the one or more indicators of atrial fibrillation exceed predetermined thresholds.

34. The system of claim 33 wherein the one or more indicators of atrial fibrillation comprise a variance of the time-varying coherence function.

35. The system of claim 34 wherein the one or more indicators of atrial fibrillation also comprise Shannon entropy.

36. The system of claim 34 wherein the predetermined thresholds are determined using receiver operator characteristic (ROC) analysis.

37. A non-transitory computer usable medium having computer readable code embodied therein, the computer readable code causing at least one processor to:
  analyze a physiological indicator signal; the physiological indicator signal being obtained from one of an image acquisition component, a photoplethysmographic (PPG) sensor and an electrocardiogram sensor;
  obtain, from said analyzing, measurements of one or more physiological parameters; and
  detect, using only the measurements of one or more physiological parameters, effects of motion artifacts in the measurements of the one or more physiological parameters;
  wherein the computer readable code, in causing the at least one processor to detect effects of motion artifacts, causes the at least one processor to:
  a. bandpass filter and detrend a segment from the measurement of one physiological parameter; wherein a bandpass filtered and detrended segment is hereinafter referred to as a preprocessed segment;
  b. obtain a value of at least one indicator of volatility, used in determining whether motion artifacts are present, for the preprocessed segment; the at least one indicator of volatility being at least Shannon entropy (SE) for the preprocessed segment; where $$SE = -\sum_{i=1}^{k} \frac{p(i)*\log(p(i))}{\log\left(\frac{1}{k}\right)}$$

and where i represents the bin number, and p(i) is the probability distribution of the preprocessed segment;
  c. include the segment in analyses of physiological measurements when comparison of the value of the at least one indicator of volatility with a predetermined threshold indicates noise/motion artifacts are not present; and
  d. select another segment of the signal from the physiological measurement and proceeding to step (a) when the value of the at least one indicator of volatility is less than a predetermined threshold and another segment is available.

38. The computer usable medium of claim 37 wherein the physiological indicator signal comprises a video color image having red, green and blue components, the video color image being an image obtained from of a portion of a subject's body; wherein the measurements of one or more physiological parameters comprise a measure of oxygen saturation; and wherein the computer readable code, in causing the at least one processor to analyze the physiological indicator signal, causes the at least one processor to:
obtain an average intensity of the red component and a blue component of the video color image of a portion of a subject's body; the average intensity of the red component and the average intensity of the blue component constituting $DC_{RED}$ and $DC_{BLUE}$ respectively;
obtain a standard deviation of the red component and the blue component; the standard deviation of the red component and the blue component constituting ACRED and ACBLUE respectively; and
obtain the measure of oxygen saturation by $$SpO2 = A - B \frac{\frac{AC_{RED}}{DC_{RED}}}{\frac{AC_{BLUE}}{DC_{BLUE}}}.$$

39. The computer usable medium of claim 37 wherein the one or more physiological measurements comprise heart rate and heart rate variability; and wherein the computer readable code, in causing the at least one processor to analyze the physiological indicator signal, causes the at least one processor to:
determine beats for the physiological indicator signal;
determine beat to beat intervals; and
apply a cubic spline algorithm to obtain a substantially continuous beat to beat interval signal indicative of heart rate.

40. The computer usable medium of claim 37 wherein the one or more physiological measurements comprise respiratory rate; and wherein the computer readable code, in causing the at least one processor to analyze the physiological indicator signal, causes the at least one processor to:
obtain time-frequency spectrum of the physiological indicator signal utilizing variable frequency complex demodulation (VFCDM); and
obtain respiratory rates by extracting a frequency component that has a largest amplitude for each time point at a heart rate frequency band.

41. The computer usable medium of claim 37 wherein the one or more physiological measurements comprise a measure of blood loss; and wherein the computer readable code, in causing the at least one processor to analyze the physiological indicator signal, causes the at least one processor to:
obtain time-frequency spectrum of the physiological indicator signal utilizing variable frequency complex demodulation (VFCDM);
obtain the amplitude modulation (AM) series from set of the largest instantaneous amplitude at each time sample within the heart rate frequency band of the time-frequency spectrum; and
determine whether the amplitude modulation decreases; a decrease in the amplitude modulation indicating blood volume loss in subject.

42. A non-transitory computer usable medium having computer readable code embodied therein, the computer readable code causing at least one processor to:
analyze the physiological indicator signal; the physiological indicator signal being obtained from one of an image acquisition component, a photoplethysmographic (PPG) sensor and an electrocardiogram sensor; wherein analysis does not include Independent Component Analysis;
obtain, from said analyzing, measurements of one or more physiological parameters; and
detect, using only the measurements of one or more physiological parameters, effects of motion artifacts in the measurements of the one or more physiological parameters; wherein the one or more physiological measurements comprise a measure of atrial fibrillation; and wherein the computer readable code, in causing the at least one processor to analyze the physiological indicator signal, causes the at least one processor to:
obtain a time-varying coherence function by multiplying two time-varying transfer functions (TVFTs), the two time-varying transfer functions obtained using two adjacent data segments, from the physiological indicator signal, one of the two adjacent data segment as an input signal and another of the two adjacent data segment as an output signal to produce a first TVTF; a second TVTF is produced by reversing the input and the output signals, using said another of the two adjacent data segment as the input signal and said one of the two adjacent data segment as the output signal; and
determine whether the time-varying coherence function is less than a predetermined quantity.

43. The non-transitory computer usable medium of claim 42 wherein the computer readable code, in causing the at least one processor to determine whether the time-varying coherence function is less than the predetermined quantity, causes the at least one processor to:
obtain one or more indicators of atrial fibrillation; and
determine whether the one or more indicators of atrial fibrillation exceed predetermined thresholds.

44. The non-transitory computer usable medium of claim 43 wherein the one or more indicators of atrial fibrillation comprise a variance of the time-varying coherence function.

45. The non-transitory computer usable medium of claim 44 wherein the one or more indicators of atrial fibrillation also comprise Shannon entropy.

46. The computer usable medium of claim 43 wherein the predetermined thresholds are determined using receiver operator characteristic (ROC) analysis.

* * * * *

UNITED STATES PATENT AND TRADEMARK OFFICE
CERTIFICATE OF CORRECTION

PATENT NO.         : 9,713,428 B2
APPLICATION NO.    : 13/354941
DATED              : July 25, 2017
INVENTOR(S)        : Ki H. Chon et al.

It is certified that error appears in the above-identified patent and that said Letters Patent is hereby corrected as shown below:

In the Claims

In Column 19, Line 51 (Claim 8), "The method of claim 1," should read -- The method of claim 7 --

In Column 22, Line 57 (Claim 28), "ACRED and ACBLUE" should read -- $AC_{RED}$ and $AC_{BLUE}$ --

In Column 25, Line 16 (Claim 38), "ACRED and ACBLUE" should read -- $AC_{RED}$ and $AC_{BLUE}$ --

Signed and Sealed this
Tenth Day of October, 2017

Joseph Matal
*Performing the Functions and Duties of the
Under Secretary of Commerce for Intellectual Property and
Director of the United States Patent and Trademark Office*